United States Patent
Lampe et al.

(10) Patent No.: US 10,866,239 B2
(45) Date of Patent: Dec. 15, 2020

(54) METHODS FOR COLON HYPERPROLIFERATIVE DISORDER DETECTION, PROGNOSIS, AND DIAGNOSIS

(71) Applicant: Fred Hutchinson Cancer Research Center, Seattle, WA (US)

(72) Inventors: Paul Lampe, Seattle, WA (US); Junghyun Rho, Auckland (NZ)

(73) Assignee: Fred Hutchinson Cancer Research Center, Seattle, WA (US)

( * ) Notice: Subject to any disclaimer, the term of this patent is extended or adjusted under 35 U.S.C. 154(b) by 0 days.

(21) Appl. No.: 15/506,466

(22) PCT Filed: Sep. 4, 2015

(86) PCT No.: PCT/US2015/048649
§ 371 (c)(1),
(2) Date: Feb. 24, 2017

(87) PCT Pub. No.: WO2016/040178
PCT Pub. Date: Mar. 17, 2016

(65) Prior Publication Data
US 2018/0224453 A1 Aug. 9, 2018

Related U.S. Application Data

(60) Provisional application No. 62/047,485, filed on Sep. 8, 2014.

(51) Int. Cl.
*G01N 33/574* (2006.01)

(52) U.S. Cl.
CPC .......... *G01N 33/57419* (2013.01); *G01N 2333/4703* (2013.01)

(58) Field of Classification Search
None
See application file for complete search history.

(56) References Cited

U.S. PATENT DOCUMENTS

| | | | |
|---|---|---|---|
| 6,372,444 B1 * | 4/2002 | Powers | C12Q 1/6886 424/9.1 |
| 2005/0009033 A1 | 1/2005 | Gray et al. | |
| 2012/0046186 A1 | 2/2012 | Pelham et al. | |

FOREIGN PATENT DOCUMENTS

| | | |
|---|---|---|
| WO | 2005/054868 A1 | 6/2005 |
| WO | 2010/004214 A1 | 1/2010 |
| WO | 2011/088226 A2 | 7/2011 |

OTHER PUBLICATIONS

Cui et al. Carcinogenesis, 2010; 31(10):1734-1741 (Year: 2010).*
Matsumoto et al. Journal of Immunology, 2010; 184:1543-1551 (Year: 2010).*
Nosho et al. British Journal of Cancer, 2005;92:1193-1200 (Year: 2005).*
Schellerer et al. American Journal of Translational Research, 2011; 3(5):445-453 (Year: 2011).*
Du et al. Clinical Cancer Research, 2008; 14(21):6751-6760 (Year: 2008).*
Mokhtari et al. Journal of Research in Medical Sciences, 2012; 17(8): 741-744 (Year: 2012).*
McKeown et al. Journal of Cancer, 2014, 5:31-43 (Year: 2014).*
Li et al., "BAG family gene and its relationship with lung adenocarcinoma susceptibility," Database Embase Elsevier Science Publishers, Amsterdam, 2010, 1 page.
Hoet et al., "Generation of high-affinity human antibodies by combining donor-derived and synthetic complementarity-determining-region diversity," *Nature Biotechnology* 23(3):344-348, 2005.
Loch et al., "Use of high density antibody arrays to validate and discover cancer serum biomarkers," *Molecular Oncology* 1:313-320, 2007.
Ozawa et al., "Enhanced Expression of Silencer of Death Domains (SODD/BAG-4) in Pancreatic Cancer," *Biochemical and Biophysical Research Communications* 271(2):409-413, 2000.
Perry et al., "Loss of giant obscurins promotes breast epithelial cell survival through apoptotic resistance," *FASEB J.* 26(7):2764-2775, 2012.
Ramirez et al., "Use of a Single-Chain Antobody Library for Ovarian Cancer Biomarker Discovery," *Molecular & Cellular Proteomics* 9:1449-1460, 2010.
Rho et al., "Discovery of sialyl Lewis A and Lewis X modified protein cancer biomarkers using high density antibody arrays," *J Proteomics* 96:291-299, 2014.

* cited by examiner

*Primary Examiner* — Vanessa L. Ford
*Assistant Examiner* — Sandra E Dillahunt
(74) *Attorney, Agent, or Firm* — Seed IP Law Group LLP; Glenda A. Gertz

(57) ABSTRACT

The present disclosure provides methods of using certain biomarker expression profiles in the detection, diagnosis, prognosis, or development of treatment regimens for various cellular hyperproliferative disorders of the bowel. For example, pre-diagnostic methods comprise detecting whether the concentration of at least BAG4 in a test biological sample from a subject is elevated as compared to a control.

16 Claims, 15 Drawing Sheets

A Antibody array analysis

Sensitivity = 0.5 at 90% specificity;
Sensitivity = 0.25 at 95% specificity;
Sensitivity = 0.156 at 98% specificity;

US 10,866,239 B2

METHODS FOR COLON HYPERPROLIFERATIVE DISORDER DETECTION, PROGNOSIS, AND DIAGNOSIS

CROSS REFERENCE TO RELATED APPLICATION

This application claims the benefit under 35 U.S.C. § 119(e) to U.S. Provisional Application No. 62/047,485 filed 8 Sep. 2014, which application is incorporated by reference herein in its entirety.

STATEMENT OF GOVERNMENT INTEREST

This invention was made with government support under CA152746 awarded by the National Institutes of Health. The government has certain rights in the invention.

BACKGROUND

Colon cancer is the third leading cause of cancer-related deaths in the US, with 142,820 new cases and 50,830 deaths reported in 2013. The 5-year survival rate is 90% when the cancer is detected at localized stages and treated by surgery. However the 5-year survival rate drops to 70% and 12% after cancer has spread to nearby or distant organs, respectively (Cancer Facts & Figures. American Cancer Society, Inc. 2013). Current guidelines recommend a colonoscopy every 10 years beginning at age 50, and fecal occult blood tests (FOBT) every year. A similar test that is currently used to screen for indicators of colon cancer is the Fecal Immunohistochemical Test (FIT). Both the FOBT and the FIT analyze occult blood in a stool sample.

Despite these guidelines, only about 50% of the recommended population is screened by endoscopy. In addition, the FOBT test is used by only about 15% of the recommended population. As a result, only 39% of colorectal cancers are detected at a localized (i.e., early) stage.

FIT has sensitivities of 55-90% for cancer and 15-44% for adenoma. FOBT has sensitivities of 50-79% for cancer and 21-35% for adenoma. However, both the FOBT test and the FIT require patient self-sampling of stool. Thus, these tests are typically performed as a home test procedure, which results in reduced patient compliance.

Accordingly, there is a need for a test that can be performed easily on a broader segment of the population with the capability of detecting hyperproliferative disorders of the colon, such as adenoma and adenocarcinoma, with reliability that is as good as or better than that of the FOBT and FIT tests. The present disclosure meets such needs, and further provides other related advantages.

DETAILED DESCRIPTION

Figure 1:
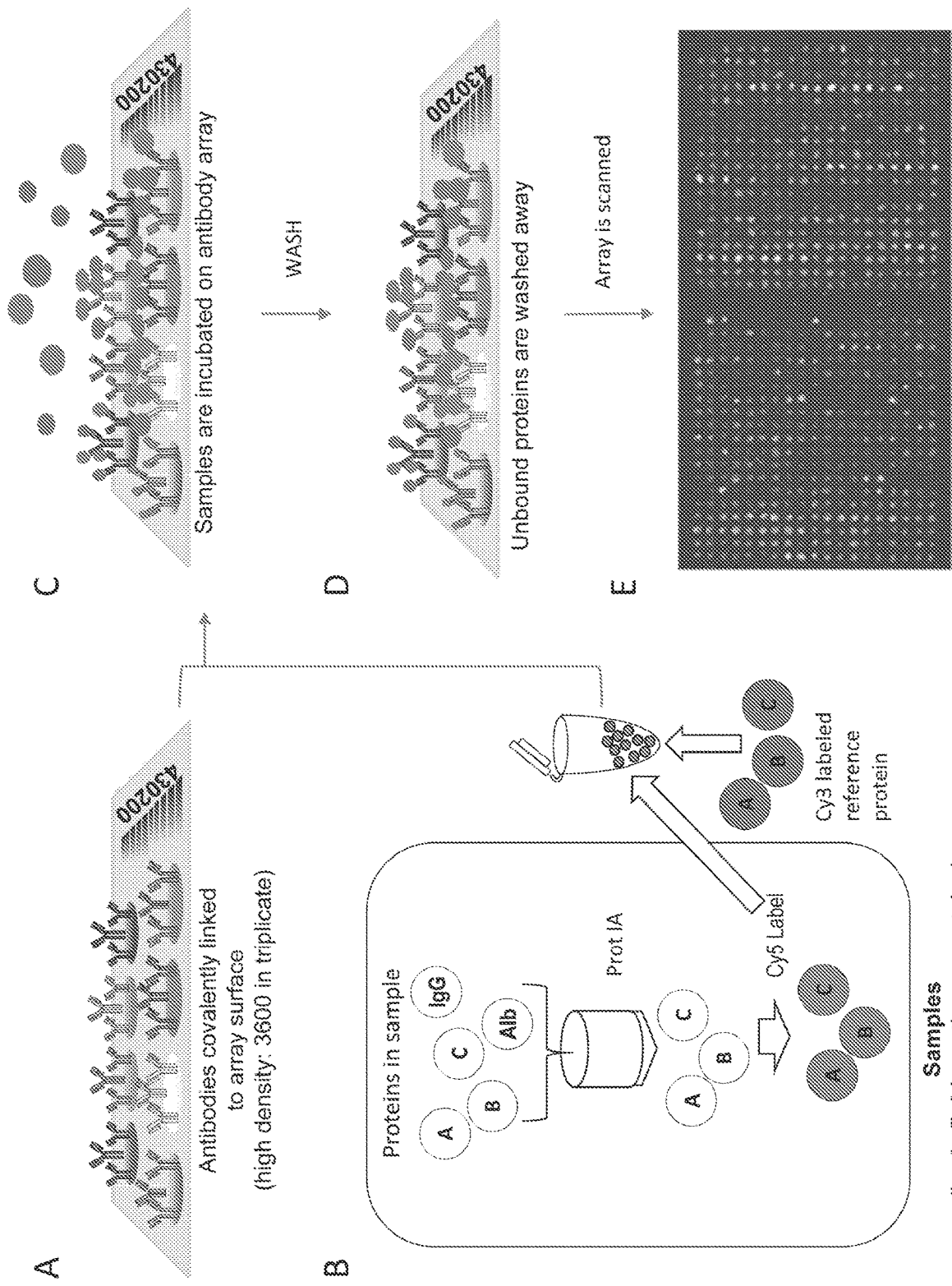
FIGS. 1A-1E show a schematic overview of the steps involved in an proteomic profiling array assay. (A) Antibodies are spotted onto slides and covalently linked via N-hydroxysuccinimide (NHS)-ester reactive groups to the slide. (B) A human biological sample (e.g., serum or plasma) containing free plasma proteins was obtained. Abundant IgG and albumin are removed from the samples before labeling the free plasma proteins. Case or control samples are labeled with Cy5 dye and a reference samples is labeled with Cy3 dye. (C) The dye-labeled plasma samples were applied onto the antibody microarray surface. (D) Only plasma proteins that bind tightly to the capture antibodies on the array will remain after washing. (E) The fluorescently labeled plasma proteins bound on antibodies are quantified by scanning the array images using an array scanner.
Figure 2:
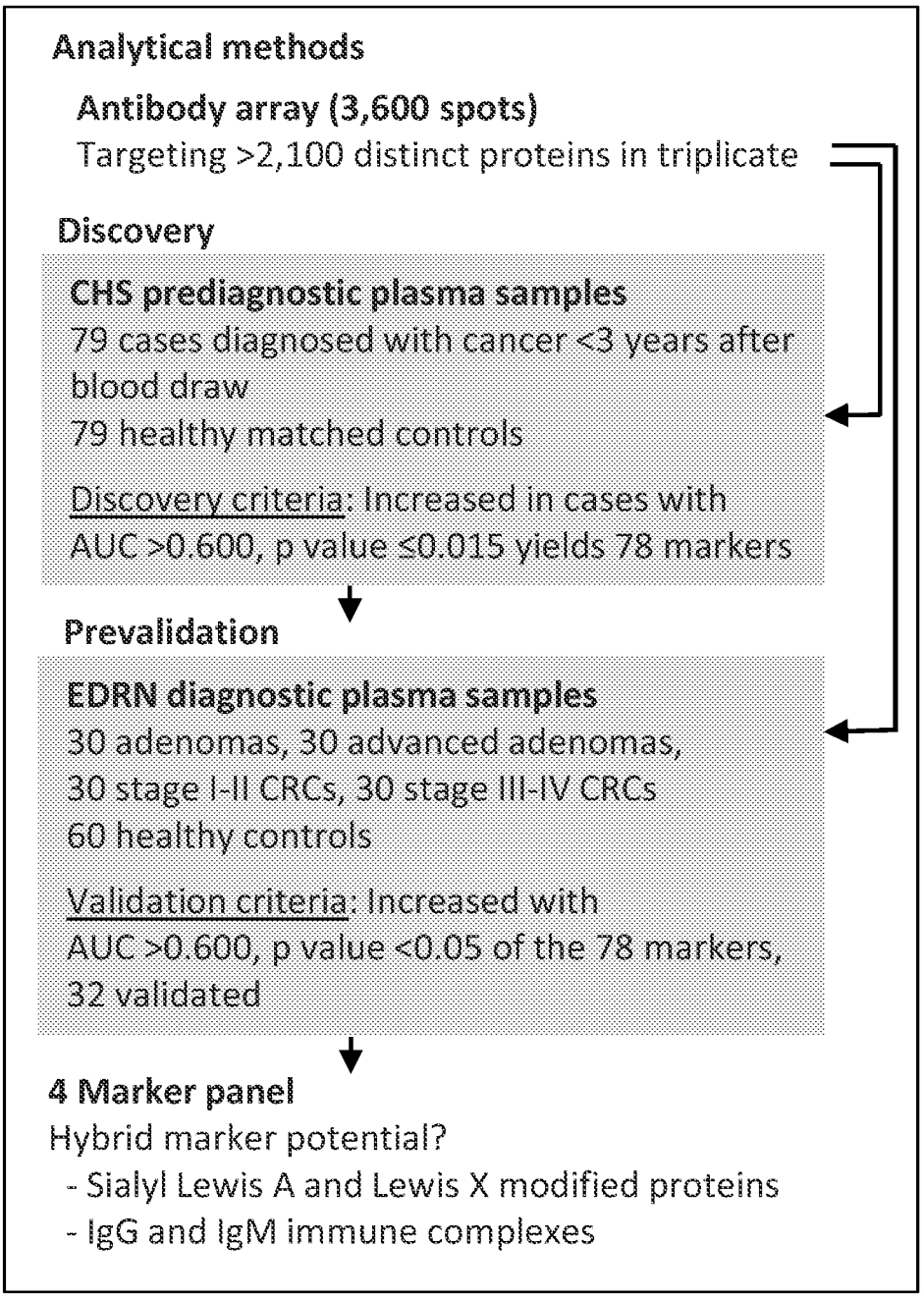
FIG. 2 depicts a schematic overview of the steps involved in identifying and validating antigens that are predictive of a colon hyperproliferative disorder.

The instant disclosure provides methods for detecting biomarkers that are elevated in subjects that are at risk for developing a colon hyperproliferative disorder (e.g., colon adenoma, colon cancer) and allows for the detection, diagnosis, prognosis, or development of treatment regimens of a colon hyperproliferative disorder. For example, the methods comprise detecting the concentration of at least one biomarker in a test biological sample from a subject and determining if the concentration of the biomarker in the test biological sample is elevated compared to a control. The concentration of the biomarker in the sample may be measured by detecting the amount of biomarker in the sample that specifically binds to a binding molecule. The methods disclosed herein can utilize an antibody array or antibody sandwich assay platform (e.g., ELISA) that allows for the isolation and detection of biomarkers if present in a sample. The biomarkers found in a biological sample, such as plasma, can be captured by antibodies specific to the biomarker and detected directly via labeling of the proteins or by antibodies that comprise a reporter (e.g., a fluorescently or chromogenically labeled antibody). The biomarkers identified herein are significantly elevated in subjects that have a colon hyperproliferative disorder. Furthermore, these methods can be combined with other known diagnostic methods for the disease of interest to further increase the sensitivity of the detection, diagnosis, prognosis or development of treatment regimens.

Therefore, the present disclosure provides powerful diagnostic tools that can be utilized to determine the risk or diagnosis of a colon hyperproliferative disorder.

Prior to setting forth this disclosure in more detail, it may be helpful to an understanding thereof to provide definitions of certain terms to be used herein. Additional definitions are set forth throughout this disclosure.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the terms "about" and "consisting essentially of" mean±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives or enumerated components. As used herein, the terms "include," "have" and "comprise" are used synonymously, which terms and variants thereof are intended to be construed as non-limiting.

As used herein, "hyperproliferative disorder" refers to any of a number of diseases that are characterized by excessive or inappropriate cell division leading to pathological changes. Neoplasia is an example of such a condition whereby abnormal cell division and tissue growth occurs more rapidly than normal and continues after the stimuli that initiated the new growth ceases. Neoplasms show partial or complete lack of structural organization and functional coordination with normal tissue and usually form a distinct mass of tissue which can be either benign (benign tumor) or malignant (cancer). Malignant tumors can occur in virtually any tissue (e.g., breast, prostate, colon, lung, skin) and are characterized by local invasion of tissue and distant metastasis often leading to death. Benign tumor growth is typically not metastatic or locally invasive, but can lead, in certain circumstances (e.g., benign polyps), to severe disease and even death due to altered tissue function or tumor growth compressing or damaging adjacent critical structures (e.g., arteries, veins, nerves).

A "colon hyperproliferative disorder" is a hyperproliferative disorder as described above that begins in tissues of the large intestine, e.g., colon. The colon is the longest part of the large intestine. Colon hyperproliferative disorders can include, for example, an adenoma, serrated adenoma, adenomatous polyp, adenocarcinoma, colon cancer, colorectal cancer, recurrent colon cancer, and neoplastic lesions. Most cases of colon cancer begin as small, noncancerous (benign) clumps of cells called adenomatous polyps. Adenomatous polyps, or adenomas, are polyps that grow on the lining of the colon and carry a significant risk of developing into cancer. The adenomatous polyp is considered pre-malignant. According to some models, over time some of these polyps can progress into colon cancers.

Cancer progression is characterized by stages. Staging is usually based on the size of the tumor, whether lymph nodes contain cancer cells, and whether the cancer has spread from the original site to other parts of the body. Stages of colon cancer include stage 0, stage I, stage II, stage III and stage IV. In some embodiments, the colon cancer is from any stage.

As used herein, "cancer recurrence" is defined as the return of cancer after treatment and after a period of time during which the cancer cannot be detected. "Recurrent colon cancer" is a colon cancer that has come back after it has been treated. The cancer may come back in the colon or in other parts of the body, such as the liver, lungs, or both.

As used herein, "prognosis" is the likelihood of the clinical outcome for a subject afflicted with a specific disease or disorder. With regard to cancer, the prognosis is a representation of the likelihood (probability) that the subject will survive (such as for 1, 2, 3, 4 or 5 years) and/or the likelihood that the tumor will metastasize. A "poor prognosis" indicates a greater than 50% chance that the subject will not survive to a specified time point (such as 1, 2, 3, 4 or 5 years), and/or a greater than 50% chance that the tumor will metastasize. In several examples, a poor prognosis indicates that there is a greater than 60%, 70%, 80%, or 90% chance that the subject will not survive and/or a greater than 60%, 70%, 80% or 90% chance that the tumor will metastasize. Conversely, a "good prognosis" indicates a greater than 50% chance that the subject will survive to a specified time point (such as 1, 2, 3, 4, or 5 years), and/or a greater than 50% chance that the tumor will not metastasize. In several examples, a good prognosis indicates that there is a greater than 60%, 70%, 80%, or 90% chance that the subject will survive and/or a greater than 60%, 70%, 80% or 90% chance that the tumor will not metastasize.

The methods disclosed herein are used to detect biomarkers that indicate the risk, diagnosis, progression, prognosis, or monitoring of a colon hyperproliferative disorder. "Biomarker" refers to a molecule, compound, or other chemical entity that is an indicator of a biological condition (e.g., disease or disorder). Exemplary biomarkers include proteins (e.g., antigens or antibodies), carbohydrates, cells, viruses, nucleic acids, or small organic molecules. For example, a biomarker may be a gene product that is (a) expressed at higher or lower levels, (b) present at higher or lower levels, (c) a variant or mutant of the gene product, or (d) simply present or absent, in a cell or tissue sample from a subject having or suspected of having a disease as compared to an undiseased tissue or cell sample from a subject having or suspected of having a disease, or as compared to a cell or tissue sample from a subject not having or suspected of having a disease. That is, one or more gene products are sufficiently specific to the test sample that one or more may be used to identify, predict, or detect the presence of disease, risk of disease, or provide information for a proper or improved therapeutic regimen. A biomarker may refer to two or more components (e.g., proteins, nucleic acids, carbohydrates, or a combination thereof) that bind together or associate non-covalently to form a complex.

The term "polypeptide" as used herein refers to a compound made up of amino acid residues that are linked by peptide bonds. The term "protein" may be synonymous with the term "polypeptide" or may refer, in addition, to a complex of two or more polypeptides. Generally, polypeptides and proteins are formed predominantly of naturally occurring amino acids.

A "binding domain" or "binding region," as used herein, refers to a protein, polypeptide, oligopeptide, or peptide (e.g., antibody, receptor) that possesses the ability to specifically recognize and bind to a target (e.g., antigen, ligand). A binding domain includes any naturally occurring, synthetic, semi-synthetic, or recombinantly produced binding partner for a biological molecule or another target of interest. Exemplary binding domains include single chain antibody variable regions (e.g., domain antibodies, sFv, single chain Fv fragment (scFv), Fab, F(ab')$_2$), receptor ectodomains, or ligands. A variety of assays are known for identifying binding domains of the present disclosure that specifically bind a particular target, including Western blot, ELISA, and Biacore® analysis.

The term "epitope" includes any protein determinant capable of specific binding to an immunoglobulin or receptor (e.g., T-cell receptor). Epitopic determinants usually consist of chemically active surface groupings of molecules, such as amino acids or sugar side chains, and usually have specific three dimensional structural characteristics, as well as specific charge characteristics.

Exemplary binding domains comprise immunoglobulin light and heavy chain variable domains (e.g., scFv, Fab) and are herein referred to as "immunoglobulin binding domains." In certain embodiments, a binding domain is part of a larger polypeptide or protein and is referred to as a "binding protein." An "immunoglobulin binding protein" refers to a polypeptide containing one or more immunoglobulin binding domains, wherein the polypeptide may be in the form of any of a variety of immunoglobulin-related protein scaffolds or structures, such as an antibody or an antigen binding fragment thereof, a scFv-Fc fusion protein, or a fusion protein comprising two or more of such immunoglobulin binding domains or other binding domains.

Sources of binding domains include antibody variable regions from various species (which can be formatted as antibodies, sFvs, scFvs, Fabs, or soluble $V_H$ domain or domain antibodies), including human, rodent, avian, leporine, and ovine. Additional sources of binding domains include variable regions of antibodies from other species, such as camelid (from camels, dromedaries, or llamas; Ghahroudi et al., FEBS Letters 414:521, 1997; Vincke et al., J. Biol. Chem. 284:3273, 2009; Hamers-Casterman et al., Nature, 363:446, 1993 and Nguyen et al., J. Mol. Biol., 275:413, 1998), nurse sharks (Roux et al., Proc. Nat'l. Acad. Sci. (USA) 95:11804, 1998), spotted ratfish (Nguyen et al., Immunogenetics, 54:39, 2002), or lamprey (Herrin et al., Proc. Nat'l. Acad. Sci. (USA) 105:2040, 2008 and Alder et al., Nature Immunol. 9:319, 2008). These antibodies can apparently form antigen-binding regions using only heavy chain variable region, i.e., these functional antibodies are homodimers of heavy chains only (referred to as "heavy chain antibodies") (Jespers et al., Nature Biotechnol. 22:1161, 2004; Cortez-Retamozo et al., Cancer Res. 64:2853, 2004; Baral et al. Nature Med. 12:580, 2006, and Barthelemy et al. J. Biol. Chem. 283:3639, 2008).

An alternative source of binding domains for use with the methods of this disclosure includes ligand(s), extracellular domains of receptors, sequences that encode random peptide libraries or sequences that encode an engineered diversity of amino acids in loop regions of alternative non-antibody scaffolds, such as fibrinogen domains (see, e.g., Weisel et al., Science 230:1388, 1985), Kunitz domains (see, e.g., U.S. Pat. No. 6,423,498), ankyrin repeat proteins (Binz et al., J. Mol. Biol. 332:489, 2003 and Binz et al., Nature Biotechnol. 22:575, 2004), fibronectin binding domains (Richards et al., J. Mol. Biol. 326:1475, 2003; Parker et al., Protein Eng. Des. Select. 18:435, 2005 and Hackel et al., J. Mol. Biol. 381: 1238, 2008), cysteine-knot miniproteins (Vita et al., Proc. Nat'l. Acad. Sci. (USA) 92:6404, 1995; Martin et al., Nature Biotechnol. 21:71, 2002 and Huang et al. Structure 13:755, 2005), tetratricopeptide repeat domains (Main et al. Structure 11:497, 2003 and Cortajarena et al., ACS Chemical Biology 3:161, 2008), leucine-rich repeat domains (Stumpp et al. J. Mol. Biol. 332:471, 2003), lipocalin domains (see, e.g., WO 2006/095164, Beste et al. Proc. Nat'l. Acad. Sci. (USA) 96:1898, 1999 and Schonfeld et al., Proc. Nat'l. Acad. Sci. (USA) 106:8198, 2009), V-like domains (see, e.g., US Patent Application Publication No. 2007/0065431), C-type lectin domains (Zelensky and Gready, FEBS J. 272:6179, 2005; Beavil et al., Proc. Nat'l. Acad. Sci. (USA) 89:753, 1992 and Sato et al., Proc. Nat'l. Acad. Sci. (USA) 100:7779, 2003), mAb$^2$ or Fcab™ (see, e.g., PCT Patent Application Publication Nos. WO 2007/098934; WO 2006/072620), or the like (Nord et al., Protein Eng. 8:601, 1995; Nord et al., Nature Biotechnol. 15:772-777, 1997; Nord et al., European J. Biochem. 268:4269, 2001 and Binz et al., Nature Biotechnol. 23:1257, 2005).

Binding domains of this disclosure can be generated as described herein or by a variety of methods known in the art (see, e.g., U.S. Pat. Nos. 6,291,161 and 6,291,158). For example, binding domains or binding proteins of this disclosure may be identified by cloning the appropriate sequence of a ligand or of a receptor extracellular domain, or by screening a Fab phage library for Fab fragments that specifically bind to a target of interest (see Hoet et al., Nature Biotechnol. 23:344, 2005). Additionally, traditional strategies for hybridoma development using a target of interest as an immunogen in convenient systems (e.g., mice, HuMAb Mouse®, TC Mouser™, KM-Mouse®, llamas, chicken, rats, hamsters, rabbits, etc.) can be used to develop antibodies, binding domains or binding proteins of this disclosure.

A binding domain and a fusion protein thereof "specifically binds" a target if it binds the target with an affinity or $K_a$ (i.e., an equilibrium association constant of a particular binding interaction with units of 1/M) equal to or greater than $10^5$ M$^{-1}$, while not significantly binding other components present in a test sample. Binding domains (or fusion proteins thereof) may be classified as "high affinity" binding domains (or fusion proteins thereof) and "low affinity" binding domains (or fusion proteins thereof). "High affinity" binding domains refer to those binding domains with a $K_a$ of at least $10^8$ M$^{-1}$, at least $10^9$ M$^{-1}$, at least $10^{10}$ M$^{-1}$, at least $10^{11}$ M$^{-1}$, at least $10^{12}$ M$^{-1}$, or at least $10^{13}$ M$^{-1}$, preferably at least $10^8$ M$^{-1}$ or at least $10^9$ M$^{-1}$. "Low affinity" binding domains refer to those binding domains with a $K_a$ of up to $10^8$ M$^{-1}$, up to $10^7$ M$^{-1}$, up to $10^6$ M$^{-1}$, up to $10^5$ M$^{-1}$. Alternatively, affinity may be defined as an equilibrium dissociation constant ($K_d$) of a particular binding interaction with units of M (e.g., $10^{-5}$ M to $10^{-13}$ M). Affinities of binding domain polypeptides and fusion proteins according to the present disclosure can be readily determined using conventional techniques (see, e.g., Scatchard et al., Ann. N.Y. Acad. Sci. 51:660, 1949; and U.S. Pat. Nos. 5,283,173, 5,468,614, or the equivalent).

Terms understood by those in the art of antibody technology are each given the meaning acquired in the art, unless expressly defined differently herein. The term "antibody" refers to an intact antibody comprising at least two heavy (H) chains and two light (L) chains inter-connected by disulfide bonds, as well as an antigen-binding portion of an intact antibody that has or retains the capacity to bind a target molecule. A monoclonal antibody or antigen-binding portion thereof may be non-human, chimeric, humanized, or human. Immunoglobulin structure and function are reviewed, for example, in Harlow et al., Eds., Antibodies: A Laboratory Manual, Chapter 14 (Cold Spring Harbor Laboratory, Cold Spring Harbor, 1988).

The term "biological sample" includes a blood sample, biopsy specimen, tissue explant, organ culture, biological fluid or specimen (e.g., blood, serum, plasma, ascites, mucosa, lung sputum, saliva, feces, cerebrospinal fluid (CSF)) or any other tissue or cell or other preparation from a subject or a biological source. A "subject" or "biological source" may be, for example, a human or non-human animal, a primary cell or cell culture or culture adapted cell line including genetically engineered cell lines that may contain chromosomally integrated or episomal recombinant nucleic acid molecules, somatic cell hybrid cell lines, immortalized or immortalizable cell or cell lines, differentiated or differentiatable cells or cell lines, transformed cells or cell lines, or the like. In a preferred embodiment, a biological sample is from a human. By "human patient" is intended a human subject who is afflicted with, at risk of developing or relapsing with, any disease or condition associated with colon hyperproliferative disorder.

A biological sample is referred to as a "test sample" when being tested or compared to a "control." A "control," as used herein, refers to an undiseased sample from the same patient and same tissue, a sample from a subject not having or suspected of having the disease of interest, a pool of samples (e.g., including samples from two to about 100,000 subjects) from various subjects not having or suspected of having the disease of interest, or data from one or more subjects not having or suspected of having the disease of interest (e.g., a database containing information on biomarker levels from one to about 5,000 to about 10,000 to about 100,000 to about 1,000,000 or more subjects). In certain embodiments, a "test sample" is analyzed and the results (i.e., biomarker levels) compared to a "control" comprising an average or certain identified baseline level calculated from a database having data derived from a plurality of analyzed undiseased or normal samples.

A "reference" or "standard" may optionally be included in an assay, which provides a measure of a standard or known baseline level of a target molecule (e.g., "normal" level). In certain embodiments, a reference sample is a pool of samples (e.g., 2, 3, 4, 5, 6, 7, 8, 9, 10, or more samples combined) from healthy individuals (i.e., not having or suspected of having the disease of interest). In certain instances, a "test sample" and a "control sample" will be examined in an assay of the instant disclosure along with a reference sample. In these instances, the "test" and "control" samples may be collectively referred to as the "target samples" since they are being compared to a reference sample.

When referring to the level of the one or more biomarker in a test sample, "elevated" compared to a control, as used herein, means a statistically significant increase in level. In certain embodiments, the level of biomarker(s) in a test sample is elevated compared to a control in a statistically significant manner. In further embodiments, the level of biomarker(s) in a test sample is increased in a statistically significant manner. For example, the difference between test and control levels may be about 2-fold, about 2.5-fold, about 3-fold, about 3.5-fold, about 4-fold, about 4.5-fold, about 5-fold, about 5.5-fold, about 6-fold, about 6.5-fold, about 7-fold, about 7.5-fold, about 8-fold, about 8.5-fold, about 9-fold, about 9.5-fold, about 10-fold, about 15-fold, about 20-fold, about 30-fold, or more. In certain instances, a statistically significant difference includes when a biomarker is present in a test sample but is absent or undetectable in the control.

In certain embodiments of this disclosure, a subject or biological source may be suspected of having or being at risk for having a disease, disorder or condition, including a malignant, disease, disorder or condition. In certain embodiments, a subject or biological source may be suspected of having or being at risk for having a colon hyperproliferative disorder (e.g., colon cancer), and in certain other embodiments of this disclosure the subject or biological source may be known to be free of a risk or presence of such disease, disorder, or condition.

As used herein, "risk" is the likelihood (probability) of a subject developing a colon hyperproliferative disorder. Risk is a representation of the likelihood that subject will develop a colon hyperproliferative disorder within a period of time (such as 1, 2, 3, 4 or 5 years). A "high risk" indicates a greater than 50% chance that the subject will develop a colon hyperproliferative disorder. In several examples, a high risk indicates that there is a greater than 60%, 70%, 80%, or 90% chance that a subject will develop a colon hyperproliferative disorder. Conversely, a "low risk" indicates a less than 50% chance that the subject will develop a colon hyperproliferative disorder. In several examples, a low risk indicates that there is a less than 10%, 20%, 30%, or 40% chance of developing a colon hyperproliferative disorder.

In some embodiments, a subject is at risk because the subject belongs to a subpopulation identified by specific characteristics, such as age, gender, diet, ethnicity, or a combination thereof. A subject of a subpopulation is, for example, a human subject that is at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, or at least 70 years of age. In some embodiments, the human subject is between 50 and 70 years of age.

As used herein, "pre-diagnosis detection" refers to the detection of biomarkers prior to diagnosis of a colon hyperproliferative disorder by other methods known in the art. Examples of such methods used to diagnose colon cancer include FOBT, FIT, colonoscopy, sigmoidoscopy, barium enema, digital rectal exam, virtual colonoscopy, or biopsy.

As used herein, "colonoscopy" is a medical procedure whereby the inside of the colon is examined using a colonoscope inserted into the rectum. A colonoscope is a thin, tube-like instrument with a light, camera and a lens for viewing. It may also have the ability to remove tissue for additional examination.

The term "array" refers to an arrangement of a plurality of addressable locations or "addresses" on a device or substrate. The locations can be arranged in two-dimensional arrays, three-dimensional arrays, or other matrix formats. The number of locations may range from two to several (e.g., 3, 4, 5, 10, 15, 20, 50, 100) to at least hundreds of thousands. Most importantly, each location represents a totally independent reaction site. A "binding protein array" refers to an array containing binding proteins, such as antibodies or other molecules containing a binding domain. An "address" on an array (e.g., a microarray) refers to a location at which a feature or element, for example, an antibody, is attached to the solid surface of the array. An array may be in any form, such as a microarray, an ELISA or a multiplex assay (e.g., xMAP® of Luminex®).

As used herein, the term "isolated" means that the molecule referred to is removed from its original environment, such as being separated from some or all of the co-existing materials in a natural environment (e.g., a natural environment may be a cell).

In certain embodiments, provided herein are methods for detecting the risk of, diagnosis of, prognosis of, or treatment plan for a colon hyperproliferative disorder by identifying the risk, diagnosis, prognosis, or treatment of the colon hyperproliferative disorder in a human subject when a test sample from the human subject has a biomarker level that is elevated compared to a control. In some embodiments, the risk, diagnosis, prognosis, or treatment of colon cancer is identified. In some embodiments, provided herein are methods for identifying a human subject in need of a colonoscopy by identifying the risk of the colon hyperproliferative disorder in a human subject when a test sample from the human subject has a biomarker level that is elevated compared to a control. In any of the embodiments disclosed herein, the level of biomarker in the sample is measured by detecting the amount of biomarker in the sample that specifically binds to a biomarker specific binding domain.

Methods to measure protein/polypeptide expression levels of selected biomarkers in the present disclosure include, but are not limited to: Western blot, immunoblot, sandwich assay (e.g., enzyme-linked immunosorbant assay (ELISA), array format), multiplex format (e.g., xMAP® from Luminex®), radioimmunoassay (RIA), immunoprecipitation, surface plasmon resonance, chemiluminescence, fluorescent polarization, phosphorescence, immunohistochemical analysis, liquid chromatography mass spectrometry (LC-MS), matrix-assisted laser desorption/ionization time-of-flight (MALDI-TOF), mass spectrometry, microcytometry, microarray, microscopy, fluorescence activated cell sorting (FACS), flow cytometry, and assays based on a property of the protein including but not limited to DNA binding, ligand binding, or interaction with other protein partners. These methods can be used to detect statistically significant difference in biomarker levels between control and test samples.

In certain embodiments, provided herein are methods for detecting the risk of a colon hyperproliferative disorder by identifying the risk of the colon hyperproliferative disorder in a human subject when a test sample from the human subject has a BAG4 antigen level that is elevated compared to a control. The level of BAG4 antigen in the sample is measured by detecting the amount of BAG4 antigen in the sample that specifically binds to a BAG4 antigen binding domain (e.g., an anti-BAG4 antibody such as SDIX, Catalog No. 2108.00.02). In some embodiments, the risk of colon adenoma is identified. In other embodiments, the risk of colon cancer is identified. In certain embodiments, the need for a colonoscopy is identified.

BAG4 is a protein that comprises approximately 457 amino acids and is normally localized to the cytoplasm of a cell. BAG4 is also referred to as BAG family molecular chaperone regulator 4, BCL-2-associated athanogene 4, and silencer of death domains (SODD). As referred to herein, "BAG4" refers to the human polypeptide represented by the reference amino acid sequence of UniProtKB No. O95429, or a variant or fragment thereof. Therefore, while full-length BAG4 can be detected in the methods disclosed herein, variants and fragments thereof also can be detected. A BAG4 antigen comprises at least a fragment or variant of BAG4 that is recognized by a BAG4 binding molecule, such as an anti-BAG4 antibody.

As used herein, "variant" means a polypeptide having a substantially similar amino acid sequence to a reference sequence. For molecules such as proteins, a variant can include an addition or deletion of one or more amino acids at one or more internal sites in the amino acid sequence of the reference enzyme and/or substitution of one or more amino acid residues at one or more sites in the amino acid sequence of the reference enzyme. The variant can result from, for example, a genetic polymorphism or human manipulation. A variant of the reference polypeptide can have at least about 40%, 45%, 50%, 55%, 60%, 65%, 70%, 75%, 80%, 85%, 90%, 91%, 92%, 93%, 94%, 95%, 96%, 97%, 98%, 99%, or more sequence identity to the amino acid sequence for the reference sequence as determined by sequence alignment programs and parameters known in the art.

As used herein, a "fragment" means a polypeptide that is lacking one or more amino acids that are found in the reference sequence. A fragment can comprise an antigen or epitope found in the reference sequence. A fragment of the reference polypeptide can have at least about 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or more of amino acids of the amino acid sequence of the reference sequence.

In certain embodiments, provided are methods for diagnosing a colon hyperproliferative disorder by diagnosing the colon hyperproliferative disorder in a human subject when a test sample from the human subject has a BAG4 antigen level that is elevated compared to a control. The level of BAG4 antigen in the sample is measured by detecting the amount of BAG4 antigen in the sample that specifically binds to a BAG4 antigen binding molecule. In some embodiments, a colon adenoma is diagnosed. In other embodiments, a colon cancer is diagnosed.

In certain embodiments, provided are methods of identifying a human subject in need of a colonoscopy, comprising identifying the human subject when a test sample from the human subject has a BAG4 antigen level that is elevated compared to a control, wherein the level of BAG4 antigen in the sample is measured by detecting the amount of BAG4 antigen in the sample that specifically binds to a BAG4 antigen binding molecule.

In any of the embodiments disclosed herein, the method can further comprise the detection of at least one of an IL6ST biomarker, a Von Willebrand Factor (VWF) biomarker, a CD44 biomarker, and an epidermal growth factor receptor (EGFR) biomarker.

In some embodiments, any of the methods described herein further comprise detecting an elevated level of an additional biomarker compared to a control wherein the additional biomarker is selected from IL6ST, VWF, CD44, EGFR, or any combination thereof. Accordingly, BAG4 and at least 1, 2, 3, or 4 of the biomarkers in the sample may be elevated compared to the control. In further embodiments, BAG4 and at least two of the IL6ST, VWF, CD44, and EGFR antigens in the test sample can have a level that is elevated compared to the control. The at least two antigens (in addition to BAG4) can be selected from IL6ST/VWF, IL6ST/CD44, IL6ST/EGFR, VWF/CD44, VWF/EGFR, CD44/EGFR, or any combination thereof.

Accordingly, the panel or plurality of antigens detected in the test sample can be BAF4/IL6ST/VWF, BAF4/IL6ST/CD44, BAF4/IL6ST/CD44:SLeA, BAF4/IL6ST/CD44:

SLeX, BAF4/IL6ST/EGFR, BAF4/IL6ST/EGFR:SLeA, BAF4/IL6ST/EGFR:SLeX, BAF4/VWF/CD44, BAF4/VWF/CD44:SLeA, BAF4/VWF/CD44:SLeX, BAF4/VWF/EGFR, BAF4/VWF/EGFR:SLeA, BAF4/VWF/EGFR:SLeX, BAF4/CD44/EGFR, BAF4/CD44:SLeA/EGFR, BAF4/CD44:SLeX/EGFR, BAF4/CD44/EGFR:SLeA, BAF4/CD44/EGFR:SLeX, BAF4/CD44:SLeA/EGFR:SLeA, BAF4/CD44:SLeA/EGFR:SLeX, BAF4/CD44:SLeX/EGFR:SLeX, BAF4/IL6ST/VWF/CD44, BAF4/IL6ST/VWF/CD44:SLeA, BAF4/IL6ST/VWF/CD44:SLeX, BAF4/IL6ST/VWF/EGFR, BAF4/IL6ST/VWF/EGFR:SLeA, BAF4/IL6ST/VWF/EGFR:SLeX, or any combination thereof. The biomarkers can be detected simultaneously or sequentially.

IL6ST is also referred to as Interleukin 6 Signal Transducer, GP130, and Oncostatin M Receptor. Three isoforms of IL6ST are known. Isoform 1 comprises approximately 918 amino acids, isoform 2 comprises approximately 329 amino acids, and isoform 3 comprises approximately 857 amino acids. As referred to herein, "IL6ST" refers to the human polypeptide represented by any one of or combination of the reference amino acid sequences of UniProtKB Nos. P40189, P40189-2, P40189-3, or variants or fragments thereof. Therefore, while full-length IL6ST can be detected in the methods disclosed herein, variants and fragments thereof also can be detected. An IL6ST antigen comprises at least a fragment or variant of IL6ST that is recognized by a IL6ST binding molecule.

VWF is protein that is known to be important in the maintenance of hemostasis, it promotes adhesion of platelets to the sites of vascular injury by forming a molecular bridge between sub-endothelial collagen matrix and platelet-surface receptor complex GPIb-IX-V. VWF comprises 2813 amino acids. As referred to herein, "VWF" refers to the human polypeptide represented by the reference amino acid sequence of UniProtKB No. P04275, or a variant or fragment thereof. Therefore, while full-length VWF can be detected in the methods disclosed herein, variants and fragments thereof also can be detected. A VWF antigen comprises at least a fragment or variant of VWF that is recognized by a VWF binding molecule.

Cluster of differentiation 44 (CD44) is known to mediate cell-cell and cell-matrix interactions through its affinity for hyaluronic acid (HA), and possibly also through its affinity for other ligands such as osteopontin, collagens, and matrix metalloproteinases (MMPs). The canonical sequence of CD44 comprises 742 amino acids. As referred to herein, "CD44" refers to the human polypeptide represented by the reference amino acid sequence of UniProtKB No. P16070, P16070-2, P16070-3, P16070-4, P16070-5, P16070-6, P16070-7, P16070-8, P16070-9, P16070-10, P16070-11, P16070-12, P16070-13, P16070-14, P16070-15, P16070-16, P16070-17, P16070-18, P16070-19, or variants or fragments thereof. Therefore, while full-length CD44 can be detected in the methods disclosed herein, variants and fragments thereof also can be detected. A CD44 antigen comprises at least a fragment or variant of CD44 that is recognized by a CD44 binding molecule.

EGFR is also referred to in the art as ERBB, ERBB1, and HER1. EGFR is a transmembrane glycoprotein that is a member of the protein kinase superfamily and has been previously shown to play well established roles in several cancers as a promoter of cell proliferation. There are at least four isoforms of EGFR. The canonical sequence of EGFR comprises 1210 amino acids. As referred to herein, "EGFR" refers to the human polypeptide represented by the reference amino acid sequence of UniProtKB No. P00533, P00533-2, P00533-3, P00533-4, or variants or fragments thereof. Therefore, while full-length EGFR can be detected in the methods disclosed herein, variants and fragments thereof also can be detected. An EGFR antigen comprises at least a fragment or variant of EGFR that is recognized by an EGFR binding molecule.

In certain embodiments, any of the methods disclosed herein can detect additional biomarkers of interest, such as, ANKRD6, BIRC3, BRCA1, BTG1, CC2D1A, CD4, CHEK1, ERCCS, FLT3, FN1 (Ab1), FN1 (Ab2), GRB2, GRN, HOXA3, LYDP1, MAPK1, MSMB, NAIP, PHB, PIK3CA, PRL, RAB7L1, SPP1, SV2A, UBE2S, VIP, WDR1, or any combination thereof.

In some embodiments, the detection of CD44 or EGFR antigen further comprises detecting a glycosylation found on the antigens. Examples of glycosylations include a sialyl Lewis A (SLeA) or a sialyl Lewis X (SLeX). Methods for detecting SLeA and SLeX antigens are known in the art (see Rho et al. (2013) *J. of Proteomics* 96:291-99). As an example, antibodies directed to CD44 or EGFR are allowed to bind the respective biomarkers. Further, labeled anti-SLeA or anti-SLeX antibodies are incubated with the biomarkers. Biomarkers that are bound by both antibodies are then differentiated from antigens that are bound by only one antibody or no antibody.

In further embodiments, the biomarkers are detected with a labeled anti-human immunoglobulin. In still further embodiments, the anti-human immunoglobulin comprises a fluorescent label, such as a cyanine dye, a coumarin, a rhodamine, a xanthenes, a fluorescien or sulfonated derivatives thereof, or a fluorescent protein. Alternately, the immunoglobulin can comprise a chromogenic reporter, such as horseradish peroxidase and an alkaline phosphatase. In yet further embodiments, the labeled anti-human immunoglobulin is an anti-IgA, anti-IgD, anti-IgE, anti-IgG, or anti-IgM.

Furthermore, any of the aforementioned methods can be combined with other known diagnostic methods for the disease of interest to further increase the sensitivity of the detection, diagnosis, prognosis or development of treatment regimens. For example, for colon cancer, a fecal blood test, colonoscopy, or a combination thereof may be used with the methods of the instant disclosure.

If the result of performing the methods described herein indicates an increased risk or diagnosis of a colon hyperproliferative disorder, then a physician can then perform a colonoscopy on the human subject to confirm the presence of a colon hyperproliferative disorder.

In other embodiments, described herein are methods for treating a colon hyperproliferative disorder, comprising administering to a human subject an effective therapeutic regimen for a human subject, wherein the colon hyperproliferative disorder is diagnosed by a method comprising identifying when a test sample from the human subject has a BAG4 antigen level that is elevated compared to a control, wherein the level of BAG4 antigen in the sample is measured by detecting the amount of BAG4 antigen in the sample that specifically binds to a BAG4 antigen binding molecule. The method of diagnosis can further include detection of at least one of an IL6ST antigen, a VWF antigen, a CD44 antigen, and an EGFR antigen, or any combination thereof, compared to a control. In some embodiments, a colon adenoma is treated. In other embodiments, a colon cancer is treated.

Non-limiting examples of a therapeutic regimen includes radiation therapy, chemotherapy, adjunctive therapy, surgery, or any combination thereof. Exemplary chemotherapeutic agents include alkylating agents (e.g., alkyl sulfonates, chlorambucil, cyclophosphamide, ifosfamide, melphalan, aziridines, epoxides, busulfan, nitrosoureas, nitrogen mustards, uramustine, temozolomide), alkylating-like agents (e.g., cisplatin, oxaliplatin, carboplatin), antimetabolites (e.g., aminopterin, methotrexate, mercaptopurine, 5-fluorouracil, fludarabine, capecitabine, cytarabine, gemcitabine), taxanes (e.g., paclitaxel, docetaxel), anthracyclines (e.g., doxorubicin, daunorubicin, epirubicin, idarubicin, mitoxantrone, valrubicin), bleomycin, mytomycin, actinomycin, hydroxyurea, topoisomerase inhibitors (e.g., camptothecin, topotecan, irinotecan, etoposide, teniposide), histone deacetylase inhibitors, monoclonal antibodies (e.g., alemtuzumab, bevacizumab, cetuximab, gemtuzumab, panitumumab, rituximab, tositumomab, trastuzumab), vinca alkaloids (e.g., vincristine, vinblastine, vindesine, vinorelbine), estrogen modulators (e.g., tamoxifen, toremifene, raloxifene), megestrol, cyclophosphamide, interleukin-2, prednisone, leucovorin, aromatase inhibitors (e.g., letrozole, anastrozole, exemestane, octreotide), and anti-androgens (e.g., flutamide, casodex), interferons (e.g., interferon-α, including subtypes thereof, such as interferon-α2a). See, e.g. Cancer: Principles and Practice of Oncology, 7th Edition, Devita et al., Lippincott Williams & Wilkins, 2005, Chapters 15, 16, 17, and 63.

In certain embodiments, provided herein are methods of monitoring progression or recurrence of a colon hyperproliferative disease in a human subject, comprising detecting the level of expression of a BAG4 antigen in a sample from a human subject that has received at least one treatment for the colon hyperproliferative disease and comparing the expression of the BAG4 antigen to a control, wherein the level of BAG4 antigen in the sample is measured by detecting the amount of BAG4 antigen in the sample that specifically binds to a BAG4 antigen binding domain.

In certain embodiments, any of the methods described herein have specificity that is at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. In certain embodiments, any of the methods described herein have a sensitivity of at least about 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

In some embodiments, any of the methods described herein have specificity for colon cancer that is about 90% and a sensitivity that ranges from about 60% to about 90%. In some of these embodiments, the sensitivity for colon cancer is greater than a Fecal Immunohistochemical Test (FIT), is at least about 70%, or ranges from about 63% to about 86%. In some embodiments, any of the methods described herein have specificity for colon adenoma that is at least about 90% and sensitivity that ranges from about 60% to about 90%. In some of these embodiments, the sensitivity for colon adenoma is greater than a Fecal Immunohistochemical Test (FIT), is at least about 40%, or ranges from about 68% to about 87%. In further embodiments, any of the methods described herein have pre-diagnostic specificity for colon cancer that is about 90% and sensitivity ranging from about 30% to about 60%. In some of these embodiments the sensitivity for pre-diagnostic colon cancer ranges from about 35% to about 52%.

As used herein, "sensitivity" refers to the proportion of subjects (e.g., humans) that have a disease and test positive over the total population that have the disease (usually expressed as a percentage). For example, a human patient population that has colon cancer and detection of BAG4 (and one or more other markers such as IL6ST, VWF, CD44, or EGFR) will be a measure of the proportion of actual colon cancer positives that are correctly identified as such (e.g., the percentage of colon cancer patients who are correctly identified as having the condition). In other words, "high sensitivity" means there are few false negatives present and "low sensitivity" means there are many false negatives present.

As used herein, "specificity" refers to a measure of the proportion of subjects (e.g., humans) that correctly test negative for the disease over the total population of subjects that do not have the disease. For example, a human patient population that has colon cancer and detection of BAG4 (and one or more other markers such as IL6ST, VWF, CD44, or EGFR) measures the proportion of negatives which are correctly identified as such (e.g., the percentage of healthy people who are correctly identified as not having the condition). In other words, "high specificity" means there are few false positives present and "low specificity" means there are many false positives present.

In another aspect, the present invention provides kits comprising materials useful for carrying out diagnostic methods according to the present invention. The diagnosis procedures described herein may be performed by diagnostic laboratories, experimental laboratories, or practitioners. The invention provides kits, which can be used in these different settings. Materials and reagents for characterizing biological samples and diagnosing a colon hyperproliferative disease in a subject according to the methods herein may be assembled together in a kit. In certain aspects, a kit comprises at least one reagent that specifically detects levels of one or more biomarkers disclosed herein, and instructions for using the kit according to a method of this disclosure.

Each kit may preferably include the reagent (e.g., primary antibody specific for a biomarker, labeled anti-human immunoglobulin) that renders the procedure specific. Thus, for detecting/quantifying a biomarker, the reagent that specifically detects levels of the biomarker may be an antibody that specifically binds to the antigen of interest. A kit of the present disclosure may further comprise one or more substrates to anchor the antigen binding molecules, including microarray slides, beads, plastic tubes, or other surfaces, one or more antibodies to biomarker, labeling buffer or reagents, wash buffers or reagents, immunodetection buffer or reagents, and detection means. Protocols for using these buffers and reagents for performing different steps of the procedure may be included in the kit. The reagents may be supplied in a solid (e.g., lyophilized) or liquid form. The kits of the present disclosure may optionally comprise different containers (e.g., slide, vial, ampoule, test tube, flask or bottle) for each individual buffer or reagent. Each component will generally be suitable as aliquoted in its respective container or provided in a concentrated form. Other containers suitable for conducting certain steps of the disclosed methods may also be provided. The individual containers of the kit are preferably maintained in close confinement for commercial sale.

In certain embodiments, kits of the present disclosure further include control samples, control slides, or both. Instructions for using the kit, according to one or more methods of this disclosure, may comprise instructions for processing the biological sample obtained from a subject, or for performing the test, instructions for interpreting the results. As well as a notice in the form prescribed by a governmental agency (e.g., FDA) regulating the manufacture, use or sale of pharmaceuticals or biological products.

EXAMPLES

Example 1

Proteomic Micoarray Assay

An antibody microarray containing approximately 3,600 human-protein specific antibodies in triplicate (10,800 total spots), which were covalently immobilized to 3-D thin film surface slides (Nexterion H slide, Schott) via N-hydroxysuccinimide (NHS) ester reactive groups (FIG. 1A), was contacted with plasma samples (FIG. 1B) from either a healthy (control) patient or a patient having colon cancer. Printed antibodies were selected based on (a) differential proteomic analyses of plasma proteins from patients with colon cancer, breast cancer, pancreas cancer and ovarian cancer, (b) proteins involved in signaling, and (c) cancer related proteins.

Briefly, frozen microarray slides were equilibrated to room temperature for 30 minutes and hydrated in 0.5% TWEEN® 20 in phosphate buffered saline (PBS) and then rinsed with distilled/deionized water ($ddH_2O$). The slides were then blocked by incubation for 30 minutes with 0.3% (v/v) ethanolamine in 50 mM sodium borate pH 8, followed by 30 minutes with 1% BSA (w/v), 0.5% TWEEN® 20 in PBS. Next, the arrays were washed with 0.5% TWEEN® 20 in PBS, followed with ddH2O. Then, the arrays were dried by centrifugation at 500 rpm for 8 min in a swinging bucket rotor with a slide rack holder (Sorvall Legend RT). The antibody-printed area of the arrays was covered with a coverslip (mSeries Lifter Slips, 22×25×1 mm, Thermo Fisher Scientific, Waltham, Mass.).

Proteomic Array

To detect the proteomic profile of the plasma samples, albumin and IgG were depleted and then 200 μg of remaining protein from either a test (cancer or adenoma) sample or a control (healthy) sample was labeled with Cy5 dye (fluorescent in the red region, about 650 nm excitation and about 670 nm emission). In addition, a reference sample (i.e., a pool of plasma from seven healthy individuals) was labeled with Cy3 dye (fluorescent in the yellow-green region, about 550 nm excitation and about 570 nm emission). Equal amounts of protein of (1) control sample and reference sample were mixed, and (2) test sample and reference sample were mixed, and contacted with the array as previously described (Loch et al., *Mol. Oncol.* 1:313, 2007; Ramirez et al., *Mol. Cell. Proteomics* 9:1449, 2010). The array was washed two times for 5 minutes with 0.5% TWEEN® 20 in PBS, followed by two more washes with PBS (5 minutes each) and once with $ddH_2O$, and then dried by centrifugation. To determine background levels of signal, the array was incubated with just secondary antibodies (no test or control plasma sample added) and the resulting signals were used for background subtraction.

Glycoproteomic Profiling Array

To detect specific glycan modifications on plasma proteins, a high-density array analysis was performed using the proteomic array as described above. The analysis focused on sialyl Lewis A (CA19.9) and sialyl Lewis X, both of which are enriched in cancer. The analysis was performed as described in Rho and Lampe (2013) *J. of Proteomics* 96:291-99. Briefly, plasma proteins were labeled with Cy dyes conjugated to anti-SLeA or anti-SLeX antibodies. The labeled samples were then allowed to bind immobilized antibodies on the proteomic array as described above.

Detection

Finally, the slides were scanned on a GenePix® 4200A microarray scanner (Axon Instruments) to produce red (Alexa Fluor® 647) and green (Alexa Fluor® 546) images. Spot intensities of the scanned array images were obtained using GenePix® Pro 6.0 image analysis software. For this, the raw GenePix® Array List (GAL) file was aligned and resized to fit the individual spot features. The average pixel intensity within an array feature was used and the median value of triplicates was selected for the intensity calculation to reduce the effect of outliers.

A threshold of 3,000 intensity units (IU) after background subtraction was established as a baseline to determine the number of positive signals. The spot intensity of 3,000 IU was selected because this represents about 5.3× above the average background value for all spots prior to background subtraction, and it is a very apparent positive spot.

Example 2

Study Populations

Pre-diagnostic samples for discovery: The sample population was collected during the Cardiovascular Health Study (CHS) and a subset of patients was subsequently diagnosed with colon cancer within 24 months following a blood draw (67 cases) or within 36 months (12 cases). These cases were individually matched on the basis of age, gender, body mass index and smoking history (Table 1).

TABLE 1

Characteristics of human subjects and plasma samples of the CHS study population

| 79 matched pairs | Cases (n = 79) | | Controls (n = 79) | |
|---|---|---|---|---|
| | n | % | n | % |
| Gender | | | | |
| Male | 44 | 55.7 | 44 | 55.7 |
| Female | 35 | 44.3 | 35 | 44.3 |
| Age | | | | |
| 65-69 | 21 | 26.6 | 21 | 26.6 |
| 70-74 | 30 | 38 | 33 | 41.8 |
| 75-79 | 21 | 26.6 | 18 | 22.8 |
| >80 | 7 | 8.9 | 7 | 8.9 |
| Race | | | | |
| White | 70 | 88.6 | 70 | 88.6 |
| Black | 9 | 11.4 | 9 | 11.4 |
| BMI | | | | |
| Normal (19.0-24.9) | 33 | 41.8 | 24 | 30.4 |
| Overweight (25.0-29.9) | 27 | 34.2 | 38 | 48.1 |
| Obese (30.0-) | 19 | 24.1 | 17 | 21.5 |
| CRC diagnosed after blood draw | | | | |
| <2 years | 67 | 84.8 | | |
| >2 years, <3 years | 12 | 15.2 | | |

Diagnostic samples for pre-validation: The sample population was collected during a National Cancer Institute initiative, the Early Detection Research Network (EDRN) project by the Great Lakes and New England Clinical validation Center, MI, USA. They were collected prior to colonoscopy and diagnosed with adenomas (30 cases), advanced adenomas (30 cases, a large polyp (>1 cm) or more than three small polyps), early stage colon cancers (30 cases: 11 I, 17 IIa, and 2 IIb stages) and late stage colon cancers (30 cases: 6 IIIa, 10 IIIb, 5 IIIc, and 9 IV stages). Plasma samples from healthy controls were collected prior to surveillance colonoscopy (30 controls) and screening colonoscopy (30 controls) (Table 2).

TABLE 2

Characteristics of human subjects and plasma samples of the EDRN study population

|  | Adenomas (n = 60) | | CRC (n = 60) | | Controls (n = 60) | |
| --- | --- | --- | --- | --- | --- | --- |
|  | n | % | n | % | n | % |
| Gender | | | | | | |
| Male | 29 | 48.3 | 34 | 56.7 | 16 | 26.7 |
| Female | 31 | 51.7 | 26 | 43.3 | 44 | 73.3 |
| Age | | | | | | |
| 30-39 | 1 | 1.7 | 1 | 1.7 | 3 | 5 |
| 40-49 | 2 | 3.3 | 12 | 20 | 8 | 13.3 |
| 50-59 | 23 | 38.3 | 12 | 20 | 30 | 50 |
| 60-69 | 21 | 35 | 13 | 21.7 | 14 | 23.3 |
| 70-79 | 10 | 16.7 | 13 | 21.7 | 5 | 8.3 |
| >80 | 3 | 5 | 9 | 15 | 0 | 0 |
| Stages | | | | | | |
| Adenoma | 30 | 50 | | | | |
| Advanced adenoma | 30 | 50 | | | | |
| I | | | 11 | 18.3 | | |
| IIa | | | 17 | 28.3 | | |
| IIb | | | 2 | 3.3 | | |
| IIIa | | | 6 | 10 | | |
| IIIb | | | 10 | 16.7 | | |
| IIIc | | | 5 | 8.3 | | |
| IV | | | 9 | 15 | | |

Pre-diagnostic samples for validation: The sample population was collected prior to screening colonoscopy during two Cancer Prevention Research Unit studies conducted at the University of Minnesota (MN-CPRU). Plasmas from clean colons (7 cases), villous polyps (7 cases), in situ (7 cases) and invasive carcinomas (6 cases) were randomly chosen for the validation study.

Example 3

Prognostic Profiles for Colon Cancer and Colon Adenoma

In this first array assay, plasma protein biomarkers were profiled. IgG and albumin depleted plasma samples (200 µg) from colon cancer case or control samples were labeled with Cy5 dye (red) and incubated with 200 µg of a similarly depleted pooled reference sample labeled with Cy3 dye (green) to measure protein levels as described above. The Markers were ranked on ability to distinguish case plasma from control with statistical significance (FIG. 3A).

A Receiver Operating Characteristic curve (ROC curve), which is a plot of the true positive rate against the false positive rate for the different possible cutpoints of the biomarker level test, was generated and accuracy is measured by the Area Under the Curve (AUC) of the ROC curve. An area approaching the value of 1 is very accurate and an area at 0.5 or below is considered inaccurate. A ROC curve is useful because it demonstrates that there is (1) a tradeoff between sensitivity and specificity (e.g., an increase in sensitivity will generally be accompanied by a decrease in specificity); (2) the closer the curve follows the left-hand border and then the top border of the ROC space, the more accurate the test; (3) the closer the curve comes to the 45-degree diagonal of the ROC space, the less accurate the test; (4) the slope of the tangent line at a cutpoint gives the likelihood ratio (LR) for that value of the test; and (5) the AUC is a measure of the assay's accuracy.

Figure 3:
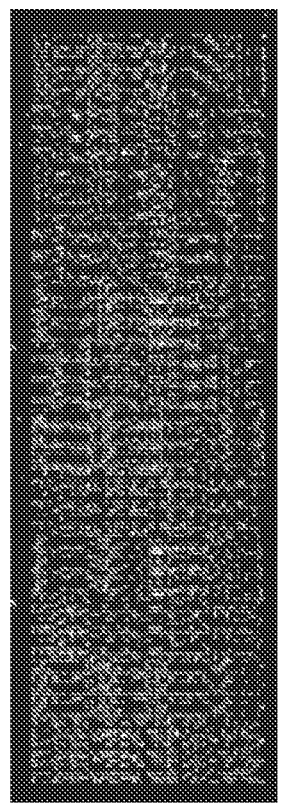
FIGS. 3A-C depict detection of antigens in control and patient samples. (A) In this first array assay, plasma protein biomarkers were profiled. IgG and albumin depleted plasma samples (200 µg) from colon cancer case or control samples were labeled with Cy5 dye (red) and incubated with 200 µg of a similarly depleted pooled reference sample labeled with Cy3 dye (green) to measure protein levels. The Markers were ranked on ability to distinguish case plasma from control with statistical significance. (B) Proteomic results from analysis of prediagnostic (<3 years prior to diagnosis) samples. (C) 32/78 upregulated candidates from discovery results were confirmed in diagnostic samples.
Figure 3:
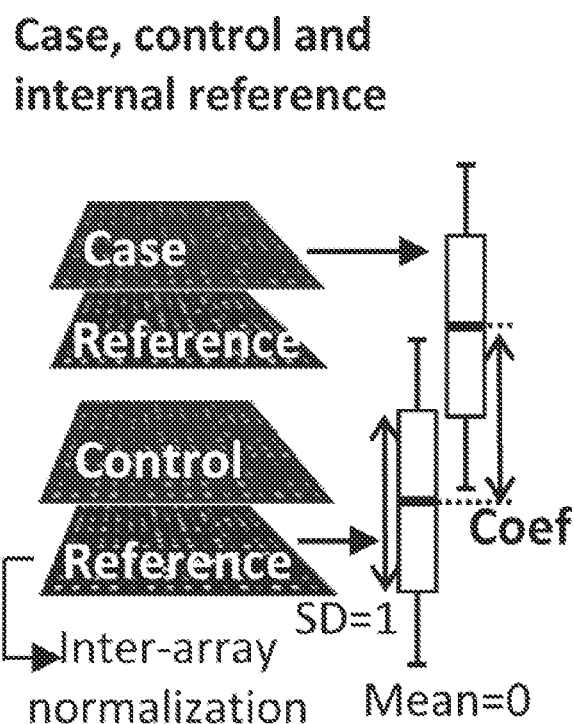
Figure 3:
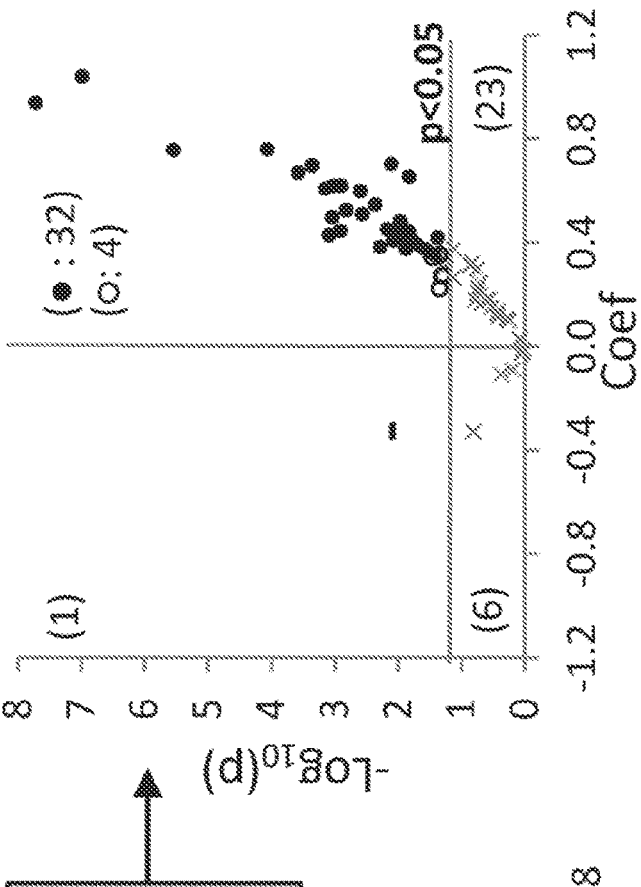
Figure 3:
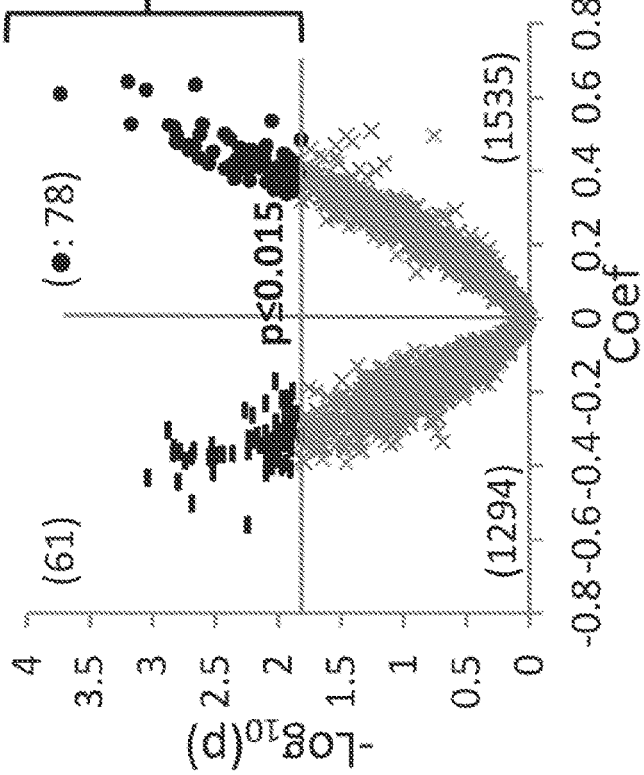

A panel of 78 biomarkers was identified as significant ($p<0.015$, AUC>0.6) in the CHS pre-diagnostic sample set (FIG. 3B). Of the 78 biomarkers, 74 were increased in the diagnostic set and 32 were subsequently validated based on the criteria that the biomarkers had increased expression in the tested cases (FIG. 3C; $p<0.05$, AUC>0.6). Therefore, a panel of 32 plasma biomarkers was identified to have prognostic value for the presence of colon adenoma or colon cancer in prediagnostic plasma samples. Table 3 shows the sensitivity, specificity, and AUC of these plasma biomarkers.

TABLE 3

Prediagnostic Biomarkers for Colon Adenoma or Colon Cancer

|  | CHS prediagnostic samples (discovery) 79 cases + 79 controls | | | | | EDRN diagnostic samples (prevalidation) 120 all cases + 60 controls | | | | | EDRN adenomas 60 cases + 60 controls | | | EDRN cancers 60 cases + 60 controls | |
| --- | --- | --- | --- | --- | --- | --- | --- | --- | --- | --- | --- | --- | --- | --- | --- |
| Proteins | Coef | p | q | AUC | Sens | Coef | p | q | AUC | Sens | Coef | p | | Coef | p |
| ANKRD6 | 0.393 | 0.012 | 0.191 | 0.609 | 18.2% | 0.483 | 0.011 | 0.015 | 0.662 | 23.4% | 0.393 | 0.051 | | 0.531 | 0.032 |
| BAG4 | 0.642 | 0.001 | 0.174 | 0.665 | 32.1% | 0.940 | 1.89E-08 | 0.003 | 0.785 | 54.2% | 1.103 | 2.30E-08 | | 0.771 | 6.84E-05 |
| BIRC3 | 0.478 | 0.002 | 0.174 | 0.655 | 14.1% | 0.510 | 0.003 | 0.006 | 0.684 | 32.2% | 0.431 | 0.027 | | 0.643 | 0.003 |
| BRCA1 | 0.408 | 0.007 | 0.191 | 0.605 | 16.7% | 0.599 | 0.003 | 0.006 | 0.697 | 35.2% | 0.540 | 0.021 | | 0.614 | 0.012 |
| BTG1 | 0.419 | 0.007 | 0.191 | 0.635 | 14.1% | 0.618 | 0.001 | 0.004 | 0.680 | 39.5% | 0.422 | 0.070 | | 0.793 | 1.12E-04 |
| CC2D1A | 0.408 | 0.012 | 0.191 | 0.617 | 20.8% | 0.757 | 2.86E-06 | 0.003 | 0.749 | 38.7% | 0.656 | 4.67E-04 | | 0.897 | 8.90E-06 |
| CD4 | 0.383 | 0.013 | 0.191 | 0.611 | 17.9% | 0.415 | 0.010 | 0.014 | 0.630 | 10.2% | 0.398 | 0.030 | | 0.334 | 0.102 |
| CD44 | 0.462 | 0.005 | 0.191 | 0.628 | 19.2% | 0.357 | 0.037 | 0.032 | 0.617 | 21.0% | 0.280 | 0.112 | | 0.480 | 0.036 |
| CHEK1 | 0.379 | 0.009 | 0.191 | 0.609 | 17.7% | 0.525 | 0.001 | 0.005 | 0.712 | 35.8% | 0.506 | 0.012 | | 0.575 | 0.004 |
| EGFR | 0.380 | 0.012 | 0.191 | 0.627 | 25.6% | 0.429 | 0.001 | 0.004 | 0.713 | 34.5% | 0.419 | 0.011 | | 0.488 | 0.006 |
| ERCC5 | 0.451 | 0.007 | 0.191 | 0.625 | 19.7% | 0.698 | 4.34E-04 | 0.003 | 0.647 | 29.7% | 0.533 | 0.022 | | 0.960 | 2.32E-05 |
| FLT3 | 0.370 | 0.008 | 0.191 | 0.635 | 15.4% | 0.409 | 0.008 | 0.012 | 0.689 | 26.9% | 0.360 | 0.074 | | 0.591 | 0.001 |
| FN1 (Ab1) | 0.427 | 0.006 | 0.191 | 0.642 | 13.0% | 0.451 | 0.007 | 0.011 | 0.716 | 34.8% | 0.368 | 0.075 | | 0.618 | 0.002 |
| FN1 (Ab2) | 0.424 | 0.012 | 0.191 | 0.629 | 13.9% | 0.430 | 0.015 | 0.018 | 0.640 | 16.9% | 0.299 | 0.145 | | 0.575 | 0.005 |
| GRB2 | 0.445 | 0.011 | 0.191 | 0.615 | 16.7% | 0.426 | 0.016 | 0.018 | 0.640 | 28.9% | 0.400 | 0.062 | | 0.448 | 0.027 |
| GRN | 0.400 | 0.010 | 0.191 | 0.637 | 13.0% | 0.446 | 0.001 | 0.004 | 0.702 | 42.1% | 0.484 | 0.007 | | 0.442 | 0.015 |
| HOXA3 | 0.429 | 0.005 | 0.191 | 0.646 | 9.2% | 0.444 | 0.015 | 0.018 | 0.650 | 17.9% | 0.343 | 0.113 | | 0.588 | 0.006 |
| IL6ST | 0.483 | 0.015 | 0.205 | 0.610 | 18.1% | 0.654 | 0.015 | 0.018 | 0.698 | 20.4% | 0.499 | 0.156 | | 1.123 | 4.10E-04 |

TABLE 3-continued

Prediagnostic Biomarkers for Colon Adenoma or Colon Cancer

| | CHS prediagnostic samples (discovery) 79 cases + 79 controls | | | | | EDRN diagnostic samples (prevalidation) 120 all cases + 60 controls | | | | | EDRN adenomas 60 cases + 60 controls | | | EDRN cancers 60 cases + 60 controls | |
|---|---|---|---|---|---|---|---|---|---|---|---|---|---|---|---|
| Proteins | Coef | p | q | AUC | Sens | Coef | p | q | AUC | Sens | Coef | p | | Coef | p |
| LYPD1 | 0.434 | 0.002 | 0.176 | 0.644 | 18.4% | 0.384 | 0.005 | 0.009 | 0.632 | 22.5% | 0.365 | 0.021 | | 0.427 | 0.021 |
| MAPK1 | 0.373 | 0.006 | 0.191 | 0.618 | 16.9% | 0.703 | 0.008 | 0.012 | 0.619 | 23.5% | 0.464 | 0.049 | | 1.260 | 1.84E−04 |
| MSMB | 0.457 | 0.005 | 0.191 | 0.643 | 16.7% | 0.394 | 0.020 | 0.021 | 0.605 | 17.5% | 0.366 | 0.089 | | 0.463 | 0.022 |
| NAIP | 0.410 | 0.008 | 0.191 | 0.635 | 13.0% | 0.375 | 0.027 | 0.026 | 0.611 | 12.1% | 0.530 | 0.006 | | 0.170 | 0.439 |
| PHB | 0.419 | 0.014 | 0.198 | 0.615 | 20.5% | 0.377 | 0.013 | 0.016 | 0.612 | 22.1% | 0.333 | 0.066 | | 0.480 | 0.012 |
| PI K3CA | 0.519 | 0.001 | 0.174 | 0.658 | 27.8% | 0.456 | 0.010 | 0.014 | 0.646 | 25.0% | 0.436 | 0.032 | | 0.490 | 0.021 |
| PRL | 0.445 | 0.006 | 0.191 | 0.625 | 13.9% | 0.760 | 8.54E−05 | 0.003 | 0.736 | 37.3% | 0.722 | 0.003 | | 0.929 | 1.28E−05 |
| RAB7L1 | 0.348 | 0.009 | 0.191 | 0.615 | 19.0% | 0.619 | 0.001 | 0.004 | 0.656 | 20.3% | 0.662 | 0.004 | | 0.571 | 0.008 |
| SPP1 | 0.416 | 0.011 | 0.191 | 0.631 | 13.9% | 0.547 | 0.004 | 0.008 | 0.664 | 31.9% | 0.376 | 0.080 | | 0.721 | 0.002 |
| SV2A | 0.405 | 0.004 | 0.191 | 0.652 | 10.4% | 0.608 | 0.001 | 0.003 | 0.709 | 37.4% | 0.577 | 0.003 | | 0.657 | 0.004 |
| UBE2S | 0.419 | 0.003 | 0.182 | 0.640 | 22.8% | 0.669 | 2.61E−04 | 0.003 | 0.674 | 41.1% | 0.489 | 0.020 | | 0.921 | 2.93E−05 |
| VIP | 0.498 | 0.002 | 0.176 | 0.643 | 22.1% | 1.043 | 1.02E−07 | 0.003 | 0.785 | 48.3% | 0.899 | 6.99E−05 | | 1.222 | 1.40E−07 |
| VWF | 0.338 | 0.011 | 0.191 | 0.622 | 25.0% | 0.419 | 0.042 | 0.035 | 0.614 | 19.5% | 0.146 | 0.519 | | 0.583 | 0.023 |
| WDR1 | 0.469 | 0.002 | 0.174 | 0.653 | 13.9% | 0.499 | 0.001 | 0.004 | 0.648 | 17.2% | 0.488 | 0.004 | | 0.533 | 0.008 |

Sens: sensitivity at 90% specificity

The following antibodies were used to validate biomarkers identified above in subsequent experiments described herein: BAG4: SDIX, cat #: 2108.00.02, lot #139A1; IL6ST: SDIX, cat #: 2048.00.02, lot #125A1; VWF: Abcam, cat #: ab6994-100, lot #: 531674; and EGFR: SDIX, cat #: 3170.00.02, lot #: R00965A01; Sialyl Lewis A: US biological CA19-9 cancer antigen, C0075-18X; and Sialyl Lewis X: BD Pharmingen, cat #551344.

Figure 4:
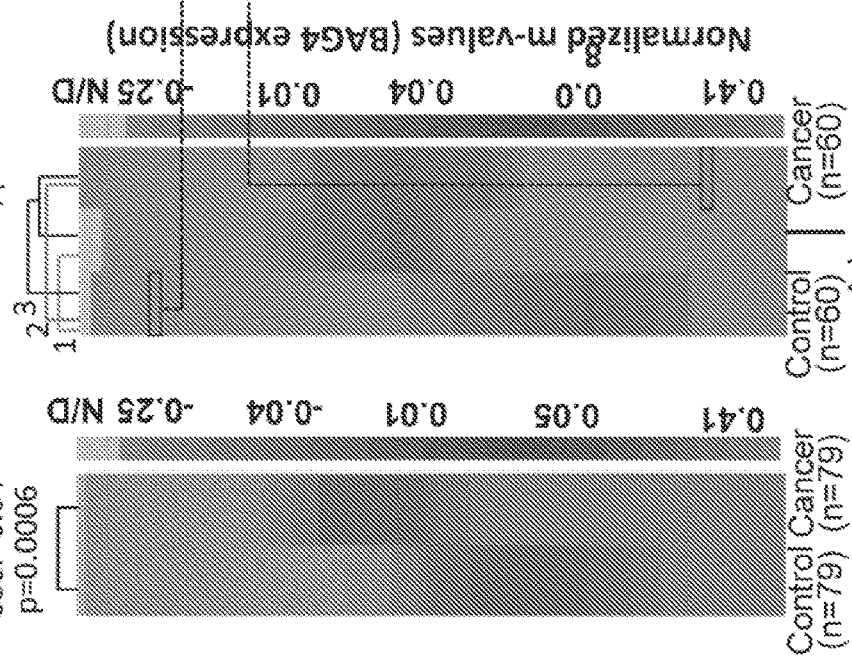
FIGS. 4A-D depicts the identification of BAG4 as a marker for colon hyperproliferative disorders. (A) shows a heat map of the BAG4 values for case and controls. (B) shows an example of the array image for the BAG4 spot of Control Sample No. 45 and Cancer Sample No. 75. (C) shows that the BAG4 antibody used on the array indeed binds to a band at the appropriate size in a western blot—i.e., this proves the specificity of the antibody for BAG4 and shows that samples with low levels of BAG4 via array also had less BAG4 protein via Western. (D) shows a third set of adenoma samples (villous, in situ, and invasive) were tested for BAG4 via western and showed increased levels of BAG4.
Figure 4:
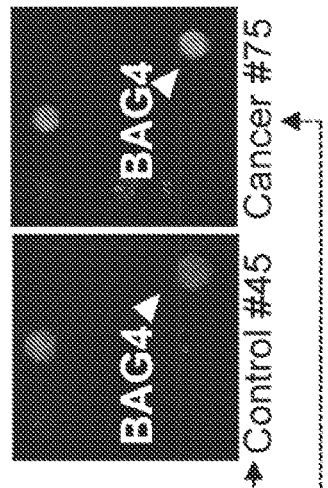
Figure 4:
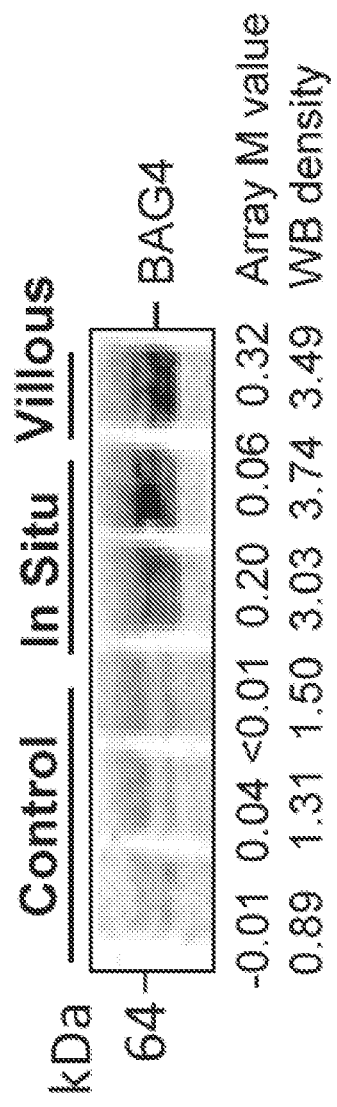
Figure 4:
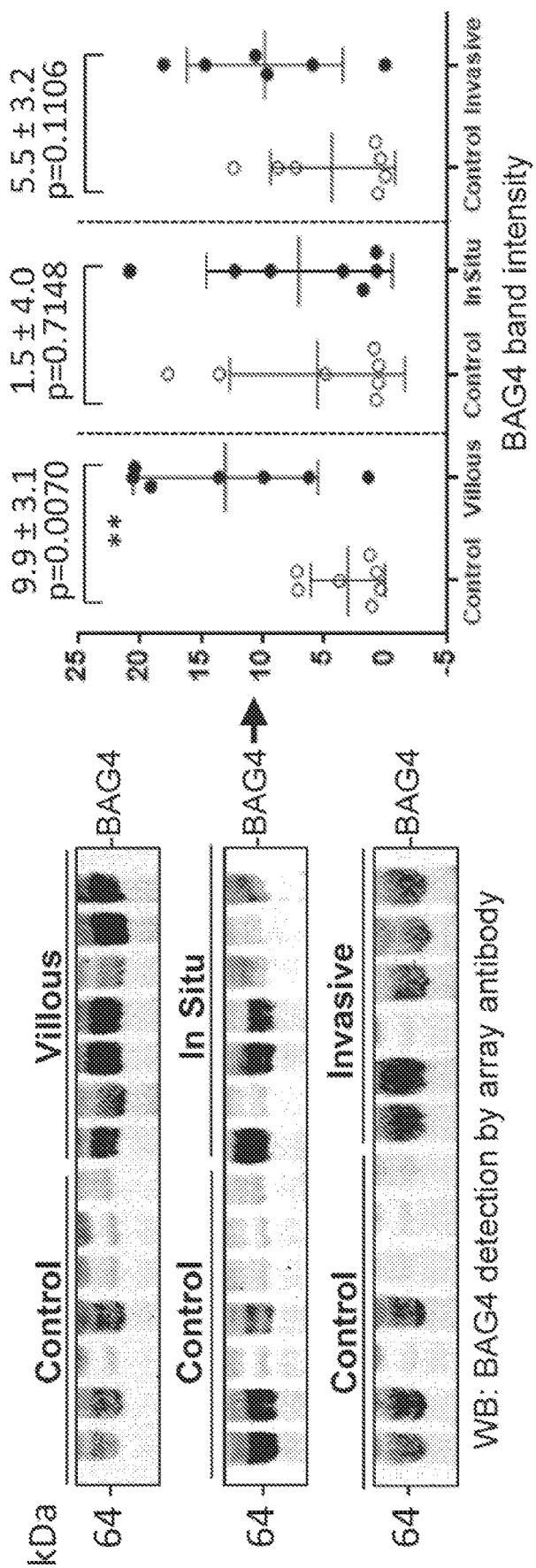

The array identified BAG4 as a candidate biomarker for colon cancer (FIGS. 4A and B). The BAG4 antibody (SDIX, Cat #2108.00.02, lot #139A1) used on the array was confirmed to bind BAG4 and demonstrated an appropriate size via a western blot (FIG. 4C). Therefore, the anti-BAG4 antibody is specific for BAG4. In addition, the data demonstrate that samples with low levels of BAG4 via array also had less BAG4 protein via Western blot.

In order to further validate the BAG4 biomarker, adenoma samples collected just prior to colonoscopy screening from the MN-CPRU study group were subjected to Western blotting using the anti-BAG4 antibody. Villous, in situ, and invasive samples showed increased levels of BAG4 (FIG. 4D).

Figure 5:
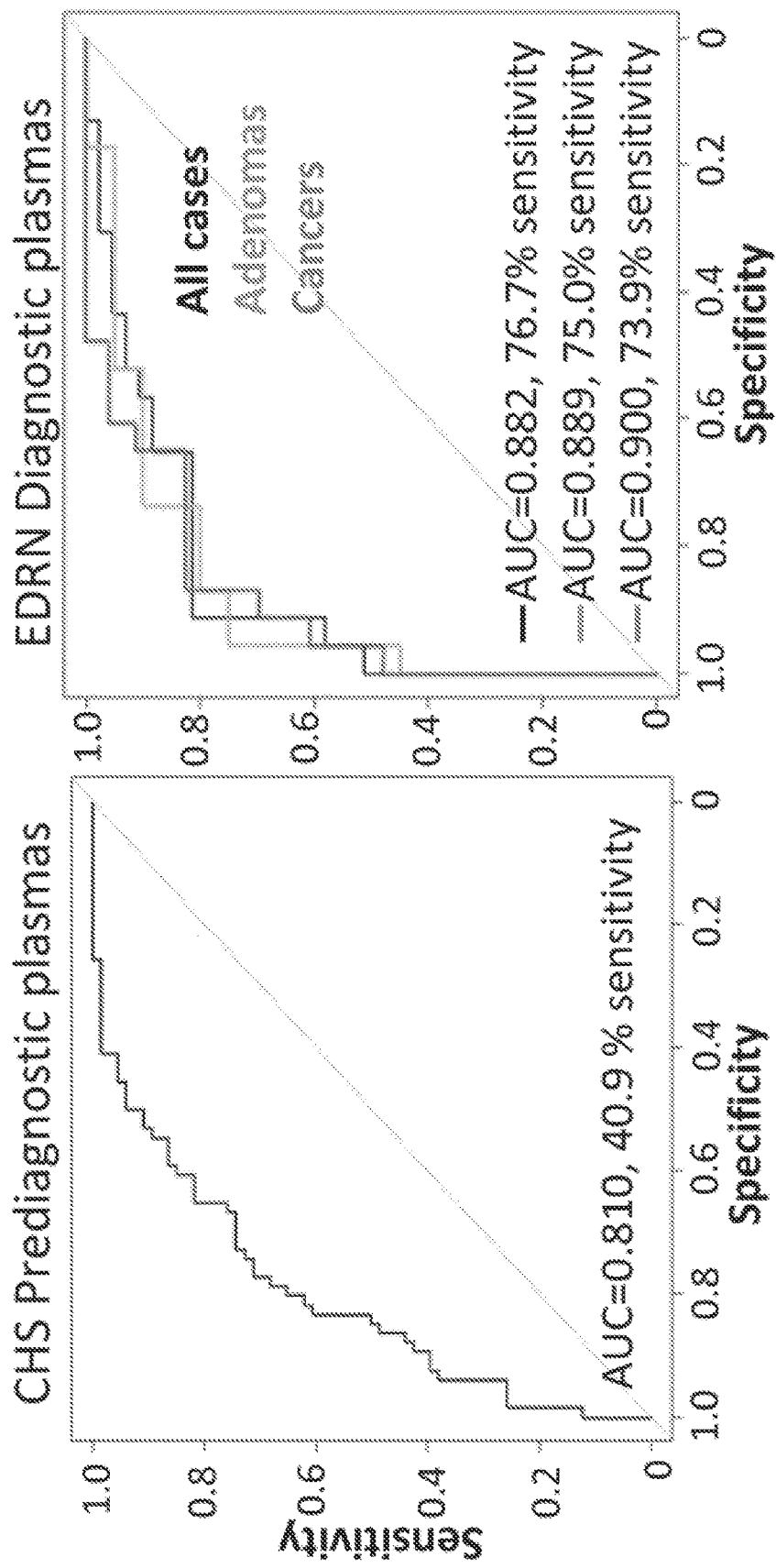
FIGS. 5A-C show the identification and validation of additional biomarkers. (A) ROC curves for a panel of BAG4, IL6ST, VWF and EGFR shows sensitivity and specificity for CHS and EDRN test samples. (B) Heat maps for IL6ST, VWF and EGFR. (C) Western blots of samples from a third set showing correct size and higher levels of proteins in adenomas than controls.
Figure 5:
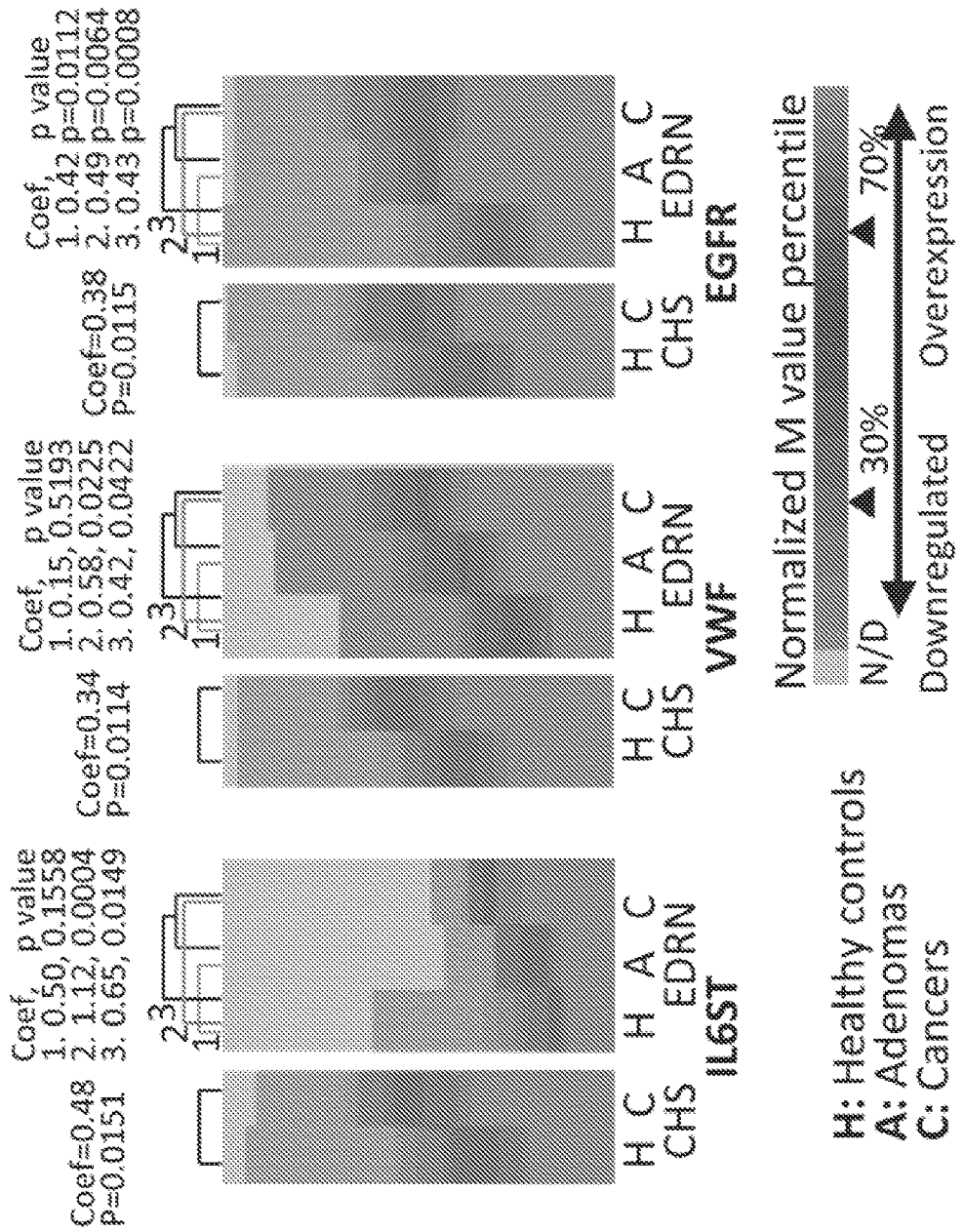
Figure 5:
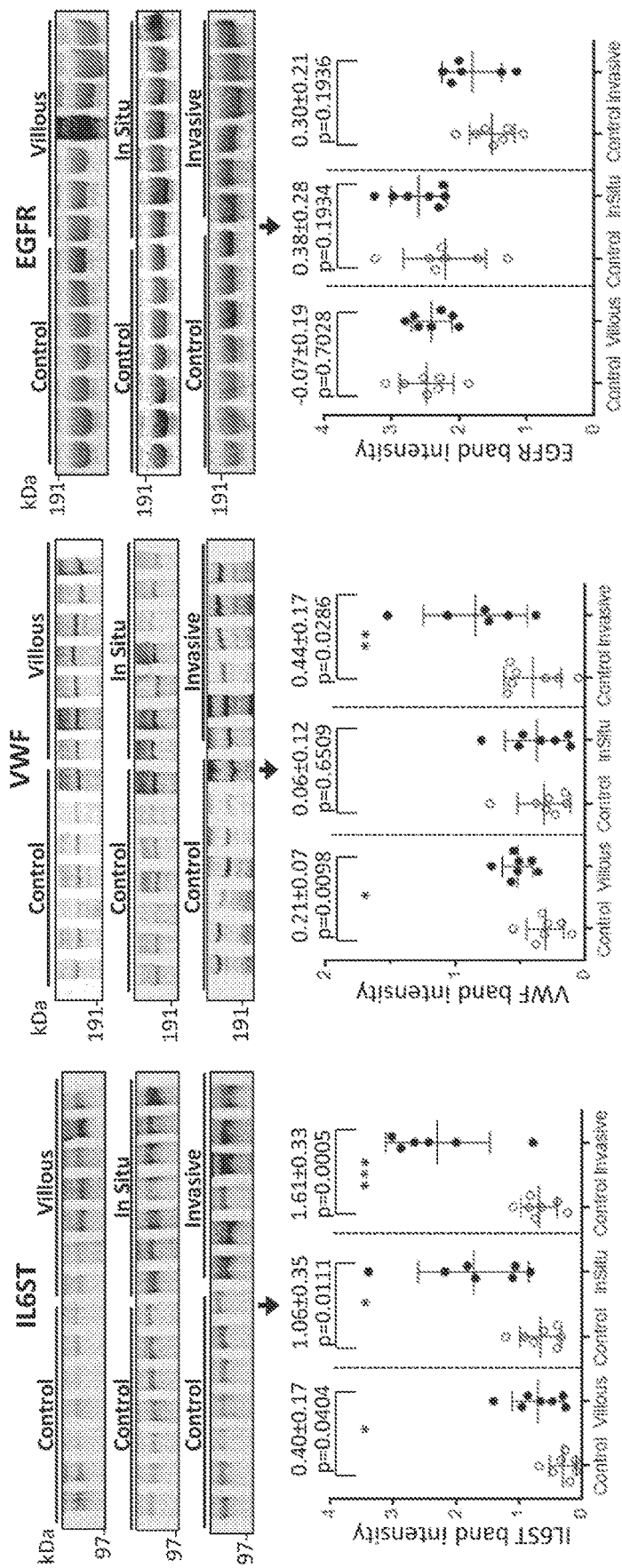

BAG4, IL6ST, VWF, and EGFR were identified as a putative panel of biomarkers for detecting adenomas and cancer in pre-diagnostic and diagnostic plasmas. ROC curves were performed on the BAG4/IL6ST/VWF/EGFR panel to determine the sensitivity and specificity (FIG. 5A). The AUC=0.810 and the sensitivity was 40% for the CHS prediagnostic plasma. In the EDRN diagnostic plasmas, for data representing all cases the AUC=0.882 and 76.7% sensitivity; in adenomas the AUC=0.889 and 75.0% sensitivity; and in cancers the AUC=0.900 and 73.9% sensitivity. Heat maps for IL6ST, VWF and EGFR demonstrate that the biomarkers are significantly overexpressed in adenoma and cancer samples (FIG. 5B). Western blots of samples from the MN-CPRU sample set were used to confirm correct size and higher levels of proteins in adenomas compared to controls (FIG. 5C).

Figure 6:
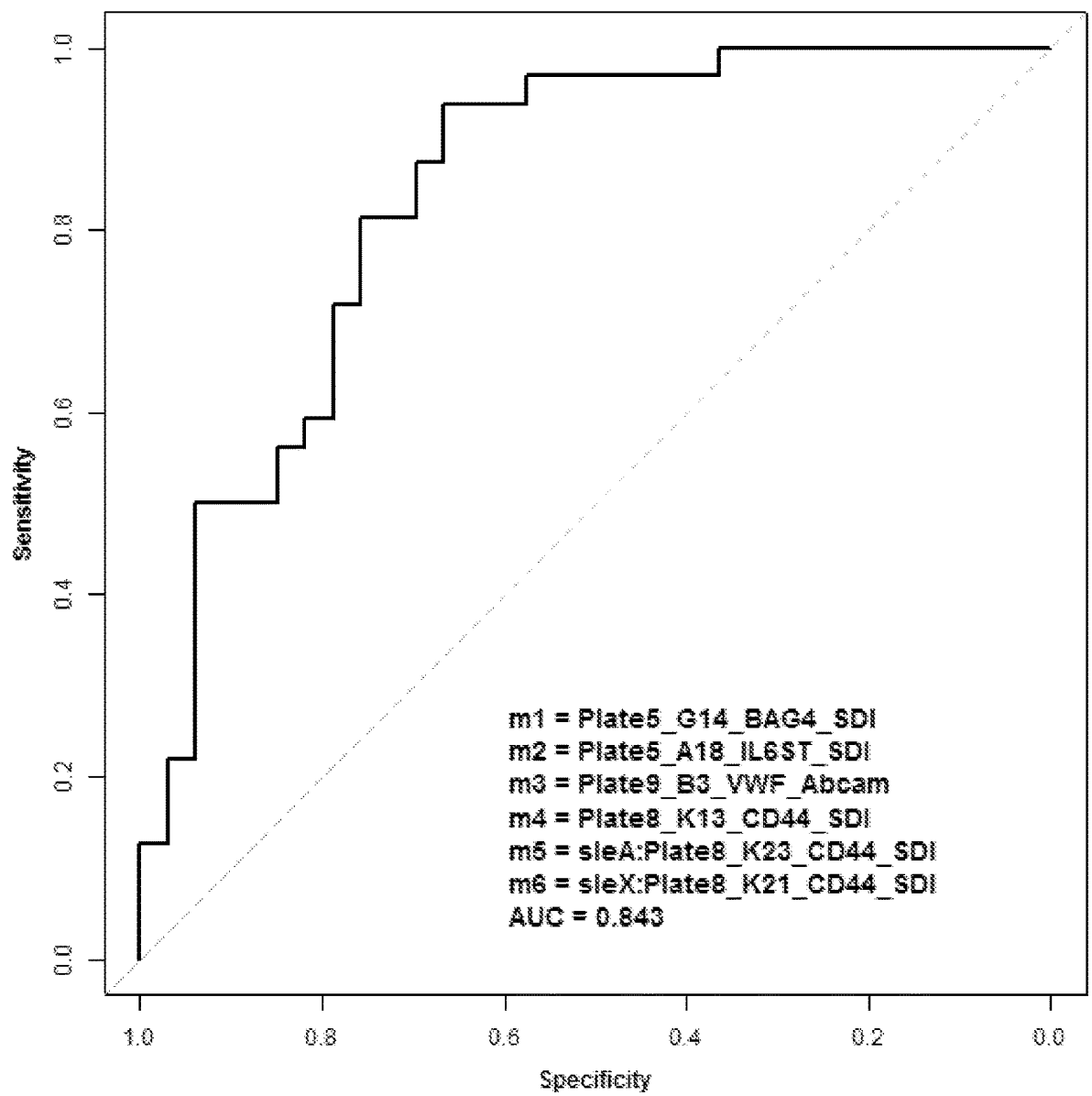
FIG. 6 depicts a ROC curve for the BAG4, IL6ST, VWF, CD44 protein and sialyl Lewis A and X content from the CHS pre-diagnostic sample set.

The top five biomarkers were divided into two four-biomarker panels that performed well. The two panels were BAG4/IL6ST/VWF/CD44 and BAG4/IL6ST/VWF/EGFR. Overall, the current panel consists of detection of the plasma biomarker proteins BAG4, IL6ST, VWF and either CD44 (glycosylated by sialyl Lewis A, or unglycosylated) or EGFR (glycosylated with either sialyl Lewis A or sialyl Lewis X, or unglycosylated). The four-biomarker panels are presented in Table 4, with the most sensitive and specific being BAG4/IL6ST/VWF/CD44 with SLeA and SLeX content (FIG. 6). These two four-marker biomarkers panels of Table 4 also showed consistently high rankings in a study comparing 60 controls, 30 early adenomas, 30 late adenomas, 30 Stage I and II, 30 Stage III and IV diagnostic samples supplied by the EDRN GI Clinical Validation Center.

TABLE 4

Results for Panel Combinations for Pre-Diagnosis of Colon Cancer

| Marker combination | | | | | Diagnostic (EDRN) | | | | | | | |
|---|---|---|---|---|---|---|---|---|---|---|---|---|
| | | | | | Prediagnostic (CHS) | All cases | | All adenoma | | Advanced adenoma + stage I-II CRC | | All cancers |
| Protein Array | Protein Array | Protein Array | Protein (+glycan) Array | Protein ELSIA | AUC Sens | AUC | Sens | AUC | Sens | AUC | Sens | AUC Sens |
| — | — | — | — | CEA | N/A  N/A | 0.576 | 26.7% | 0.495 | 15.0% | 0.537 | 20.0% | 0.656  38.3% |
| BAG4+ | IL6ST+ | VWF+ | CD44 | — | 0.792  42.4% | 0.899 | 73.2% | 0.860 | 68.4% | 0.905 | 75.0% | 0.942  81.8% |
| BAG4+ | IL6ST+ | VWF+ | CD44:SLeA | — | 0.835  44.4% | 0.900 | 79.5% | 0.881 | 72.2% | 0.919 | 85.0% | 0.946  85.7% |
| BAG4+ | IL6ST+ | VWF+ | CD44:SLeX | — | 0.781  23.4% | 0.904 | 74.4% | 0.934 | 88.9% | 0.876 | 72.2% | 0.986  95.2% |

TABLE 4-continued

Results for Panel Combinations for Pre-Diagnosis of Colon Cancer

| Marker combination | | | | | Diagnostic (EDRN) | | | | | | | | | |
|---|---|---|---|---|---|---|---|---|---|---|---|---|---|---|
| | | | | | Prediagnostic (CHS) | | All cases | | All adenoma | | Advanced adenoma + stage I-II CRC | | All cancers | |
| Protein Array | Protein Array | Protein Array | Protein (+glycan) Array | Protein ELSIA | AUC | Sens | AUC | Sens | AUC | Sens | AUC | Sens | AUC | Sens |
| BAG4+ | IL6ST+ | VWF+ | CD44:SLeA/X | — | 0.843 | 50.0% | 0.900 | 78.4% | 0.931 | 88.9% | 0.877 | 64.7% | 0.983 | 95.0% |
| BAG4+ | IL6ST+ | VWF+ | EGFR | — | 0.810 | 40.9% | 0.882 | 76.7% | 0.889 | 75.0% | 0.876 | 71.4% | 0.900 | 73.9% |
| BAG4+ | IL6ST+ | VWF+ | EGFR:SLeA | — | 0.848 | 51.6% | 0.883 | 78.6% | 0.898 | 75.0% | 0.881 | 71.4% | 0.906 | 63.6% |
| BAG4+ | IL6ST+ | VWF+ | EGFR:SIeX | — | 0.815 | 35.8% | 0.929 | 87.5% | 0.926 | 83.3% | 0.930 | 84.2% | 0.955 | 86.4% |
| BAG4+ | IL6ST+ | VWF+ | EGFR:SLeA/X | — | 0.839 | 44.6% | 0.927 | 87.2% | 0.932 | 84.2% | 0.933 | 83.3% | 0.955 | 85.7% |

Figure 7:
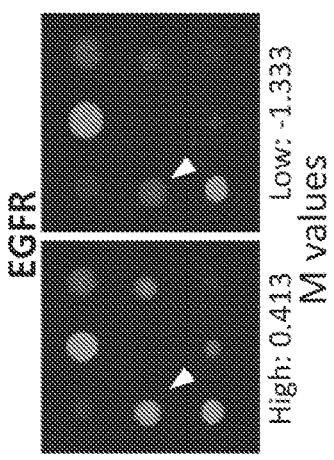
FIGS. 7A-B show confirmation that array spot intensity matches immunoblot levels. (A) Array spots for IL6ST, VWF and EFR. (B) Western immunoblots using arrayed antibodies to detect IL6ST, VWF, and EGFR.
Figure 7:
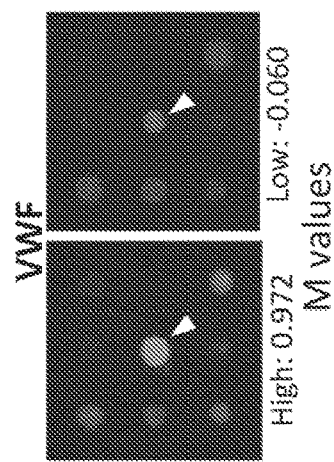
Figure 7:
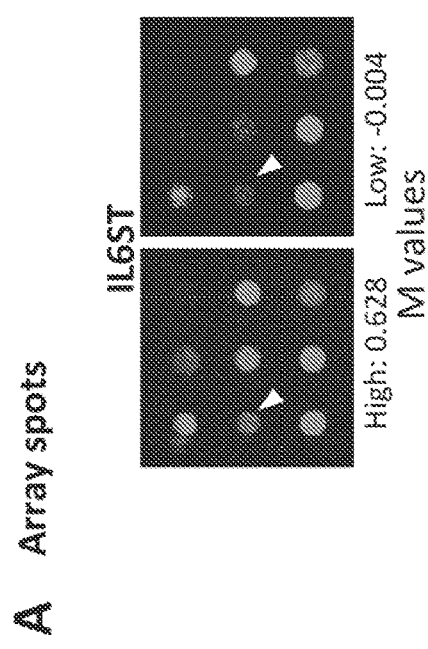
Figure 7:
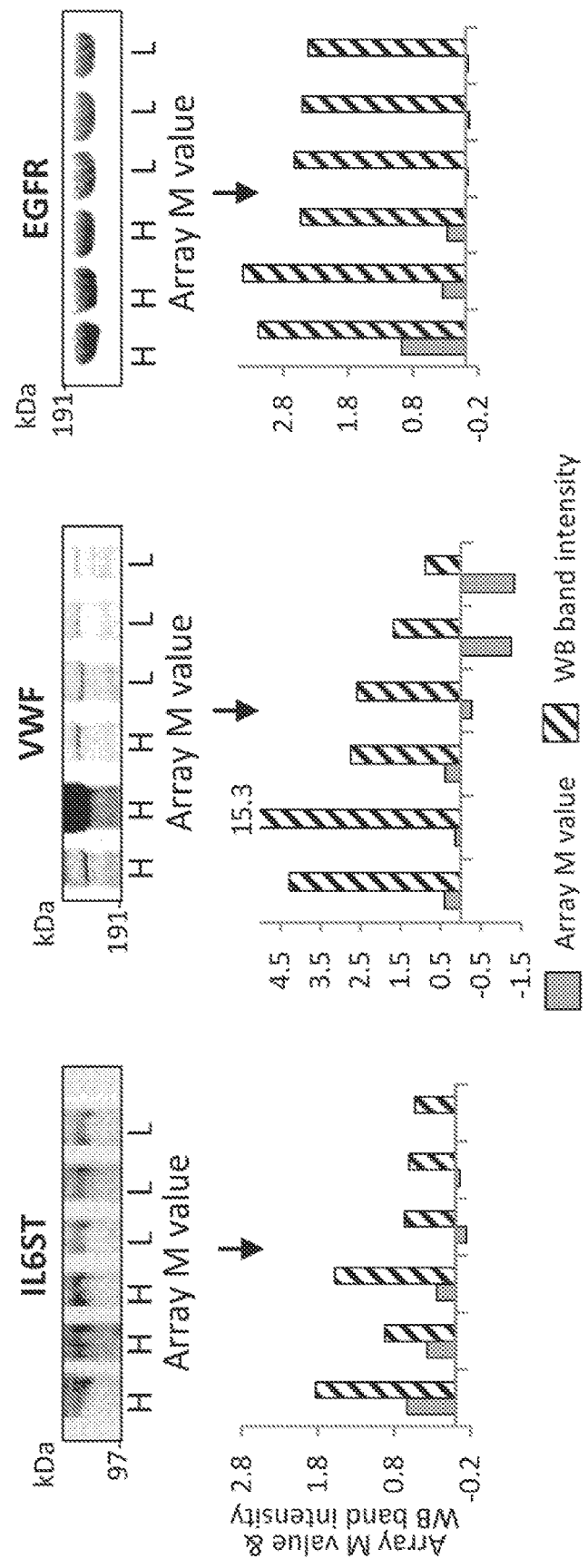

N/A: not assayed, N/C: computation not converged, Sen: sensitivity at 90% specificity The IL6ST, VWF and EGFR array antibodies were validated for its specificity in Western blotting (FIG. 7A). Six plasma samples with known M-values for each protein were used for sample preparation (30 µg per lane after albumin and IgG depletion). The blotting images show that prominent bands were identified at expected areas (IL6ST at 103 kDa, VWF at 309 kDa, and EGFR at 134 kDa). Their intensity changes agreed to their known M-value ratios as shown in the double bar graphs (FIG. 7B).

Figure 8:
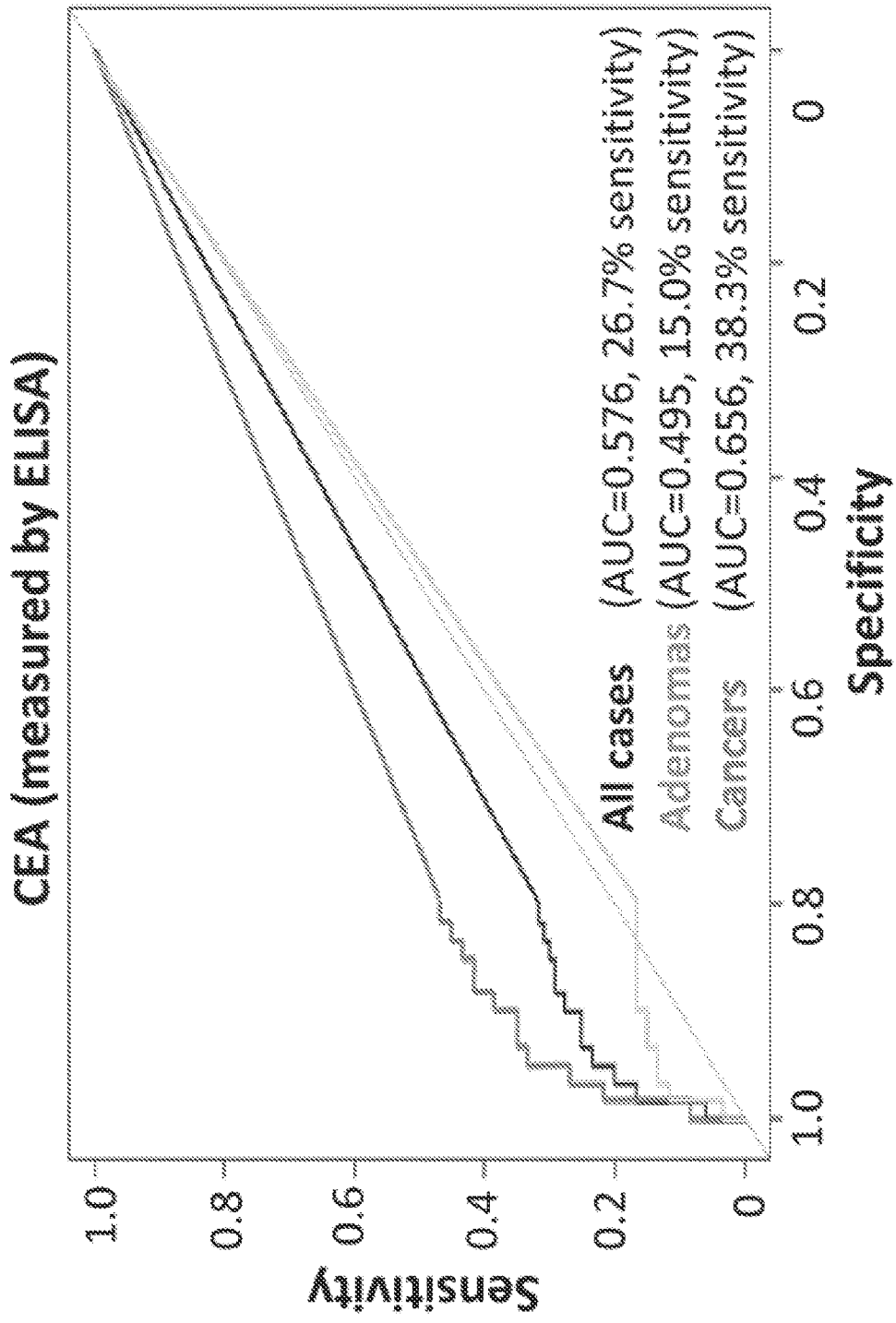
FIGS. 8A-B show ROC curves for ELISA and array assay values for the detection of antigens associated with adenomas and cancer. (A) shows sensitivity and specificity performance for carcinoembryonic antigen (CEA). (B) shows the performance of a panel of BAG4, IL6ST, VWF, EGFR:SLeA/X, and CEA.
Figure 8:
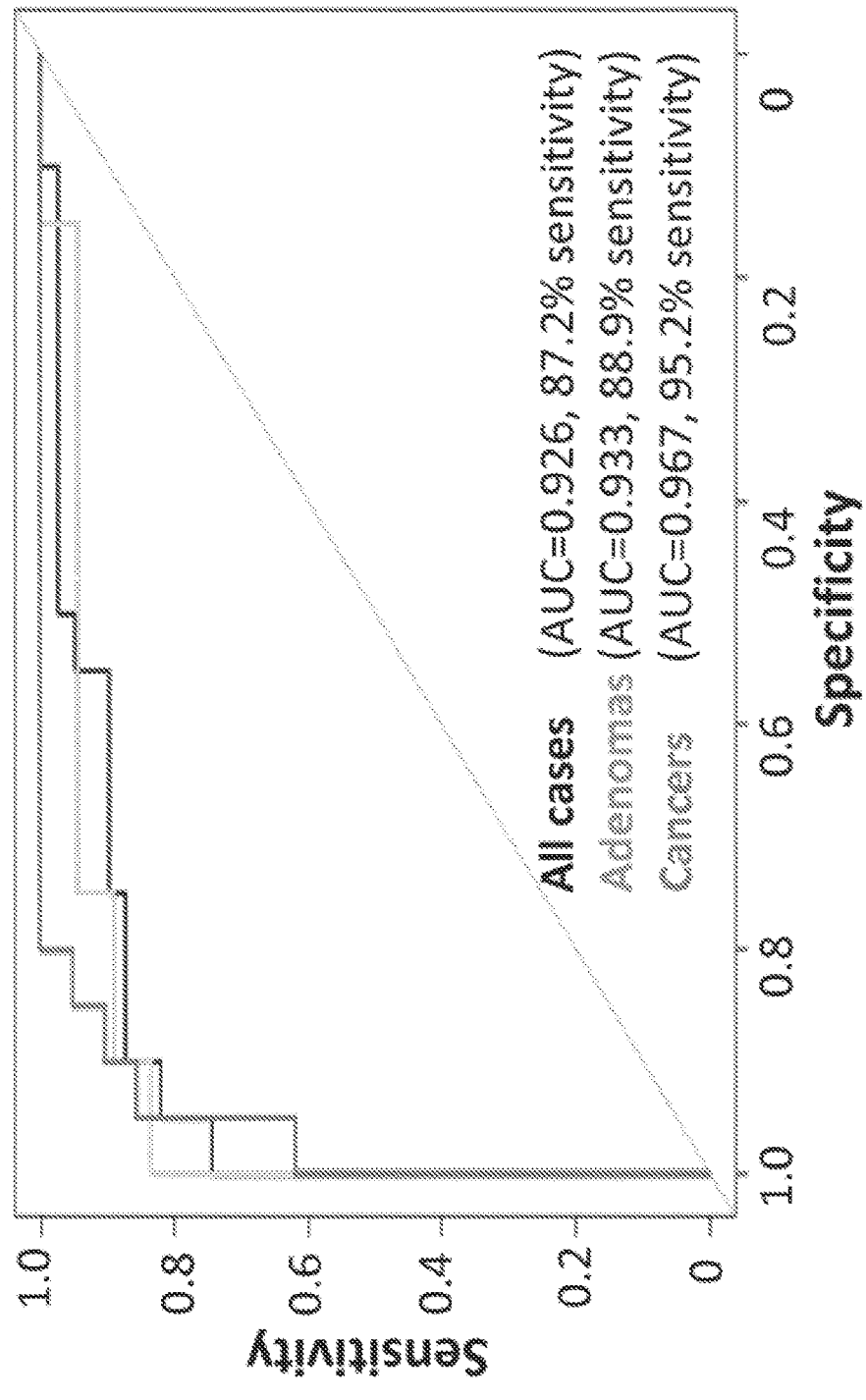

An ELISA for carcinoembryonic antigen (CEA) was performed and compared to array data from a panel of BAG4, IL6ST, VWF, EGFR:SLeA/X using ROC curves. The analysis compared adenomas, cancers, and all cases combined (FIG. 8A-B). The results for CEA demonstrated adenomas had an AUC=0.495 and sensitivity of 15.0%; cancers had an AUC=0.656 and sensitivity of 38.3%; and all cases had an AUC=0.576 and a sensitivity of 26.7%. The results for a panel of BAG4, IL6ST, VWF, EGFR:SLeA/X and CEA(ELISA) demonstrated adenomas had an AUC=0.933 and sensitivity of 88.9%; cancers had an AUC=0.967 and sensitivity of 95.2%; and all cases had an AUC=0.926 and a sensitivity of 87.2%.

The performance of the four-biomarker panel(s) compares favorably with both the FOBT and FIT fecal tests. FIT sensitivity for cancer ranges from 55%-100%; with sensitivity for adenomas ranging from 15-44%. FOBT sensitivity for cancer is 50%-79%, and has sensitivity for adenomas of between 21% and 35%.

In contrast, the currently disclosed blood test compares very favorably, providing 63-86% sensitivity for cancer and 68-87% sensitivity for adenomas (at 90% specificity); on pre-diagnostic samples from the CHS cohort, the currently disclosed panel provides a 35-52% sensitivity for cancer at a 90% specificity.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method for detecting a biomarker in a biological sample from a human subject, the method comprising:
    contacting the biological sample and a control sample with an immunoglobulin binding protein specific for BCL-2-associated athanogene 4 (BAG4) and with an immunoglobulin binding protein specific for interleukin 6 signal transducer (IL6ST), wherein the biological sample is selected from blood, serum, plasma, ascites, mucosa, lung sputum, saliva, feces, or cerebrospinal fluid;
    detecting whether a signal results from contacting the biological sample and the control sample with the immunoglobulin binding proteins and measuring the BAG4 and IL6ST signals, wherein the BAG4 signal indicates specific binding of the BAG4-specific immunoglobulin binding protein to BAG4 and the IL6ST signal indicates specific binding of the IL6ST-specific immunoglobulin binding protein to IL6ST; wherein the biological sample is from a human subject at risk of developing or having a colon hyperproliferative disorder (CHD).

2. The method of claim 1, wherein the CHD is colon adenoma or colon cancer.

3. The method according to claim 1, further comprising detecting an elevated level of an additional antigen compared to a control, wherein the additional antigen is selected from Von Willebrand factor (VWF) cluster of differentiation 44 (CD44), epidermal growth factor receptor (EGFR), or any combination thereof.

4. The method of claim 3, wherein at least two of the VWF, CD44, and EGFR antigens in the test sample have a level that is elevated compared to the control, wherein the at least two antigens are selected from VWF/CD44, VWF/EGFR, or CD44/EGFR.

5. The method of claim 3, wherein CD44 and/or EGFR is glycosylated.

6. The method of claim 5, wherein the glycosylation is a sialyl Lewis A or a sialyl Lewis X.

7. The method of claim 1, wherein the level of expression of BAG4 is at least 2, 3, 4, 5, 6, 7, 8, 9, 10, 15, or 20 fold higher than the control.

8. The method according to claim 1, wherein each of the BAG4-specific and IL6ST-specific binding proteins are individually labeled with a reporter or each is individually detected with a labeled anti-human immunoglobulin.

9. The method according to claim 8, wherein the anti-human immunoglobulin comprises a fluorescent label or a chromogenic reporter.

10. The method of claim 8, wherein the labeled anti-human immunoglobulin is an anti-IgA, anti-IgD, anti-IgE, anti-IgG, or anti-IgM.

11. The method of claim 8, wherein the method comprises a sandwich assay.

12. The method of claim 1, further comprising the step of performing a colonoscopy on the human subject to confirm the presence of a colon hyperproliferative disorder.

13. The method of claim 1, wherein the biological sample is blood, serum, or plasma.

14. The method of claim 2, wherein:
    (a) specificity for colon cancer is about 90% and sensitivity is between about 63% and about 86%;
    (b) specificity for colon adenoma is about 90% and sensitivity is between about 68% and 87%; or
    (c) pre-diagnostic specificity for colon cancer is about 90% and sensitivity is between about 35% and about 52%.

15. The method according to claim 1, wherein proteins of the biological sample are labeled with a reporter.

16. The method according to claim 1, wherein the BAG4-specific and IL6ST-specific binding proteins are antibodies and are part of an antibody array.

* * * * *